United States Patent [19]
Waldeck et al.

[11] Patent Number: 5,677,297
[45] Date of Patent: Oct. 14, 1997

[54] BENZAZEPINE-, BENZOXAZEPINE- AND BENZOTHIAZEPINE-N-ACETIC ACID DERIVATIVES, PROCESS FOR THEIR PREPARATION AND PHARMACEUTICAL COMPOSITIONS CONTAINING THEM

[75] Inventors: Harald Waldeck, Isernhagen; Dagmar Hoeltje, Gehrden; Josef Messinger, Sehnde; Jochen Antel, Bad Muender; Michael Wurl, Garbsen; Dirk Thormaehlen, Rheden, all of Germany

[73] Assignee: Solvay Pharmaceuticals GmbH, Hanover, Germany

[21] Appl. No.: 620,213

[22] Filed: Mar. 22, 1996

[30] Foreign Application Priority Data

Mar. 23, 1995 [DE] Germany .............. 195 10 566.4

[51] Int. Cl.[6] ............ A61K 31/55; C07D 267/14; C07D 281/10; C07D 487/00
[52] U.S. Cl. .................. 514/211; 514/213; 540/491; 540/523
[58] Field of Search .................. 514/211, 213; 540/491, 523

[56] References Cited

U.S. PATENT DOCUMENTS

| | | | |
|---|---|---|---|
| 5,438,046 | 8/1995 | Norcini et al. | 514/89 |
| 5,457,196 | 10/1995 | Warshawsky et al. | 540/521 |
| 5,504,080 | 4/1996 | Karanewsky | 514/214 |
| 5,506,259 | 4/1996 | Norcini et al. | 514/423 |

FOREIGN PATENT DOCUMENTS 599444   1/1994   European Pat. Off.

OTHER PUBLICATIONS

De Lombaert et al., "Pharmacological Profile of a Non-Peptidic Dual Inhibitor . . . ", *Biochemical and Biophysical Research Communications*, vol. 204, No. 1 (Oct. 14, 1994), pp. 401-412.

*Primary Examiner*—Mukund J. Shah
*Assistant Examiner*—Brenda Coleman
*Attorney, Agent, or Firm*—Evenson, McKeown, Edwards & Lenahan P.L.L.C.

[57] ABSTRACT

Compounds with neutral endopeptidase (NEP) inhibitory activity corresponding to the formula I

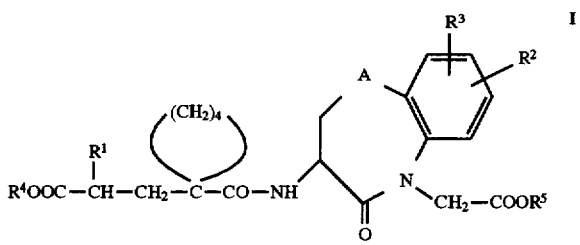

in which $R^1$ is a lower alkoxy-lower-alkyl group whose lower alkoxy radical is substituted by a lower alkoxy group, or a phenyl-lower-alkyl or phenyloxy-lower-alkyl group which can optionally be substituted in the phenyl ring by lower alkyl, lower alkoxy or halogen, or a naphthyl-lower-alkyl group, A is $CH_2$, O or S, $R^2$ is hydrogen or halogen, $R^3$ is hydrogen or halogen, $R^4$ is hydrogen or a group forming a biolabile ester, and $R^5$ is hydrogen or a group forming a biolabile ester, and the physiologically acceptable acid addition salts thereof.

14 Claims, No Drawings

BENZAZEPINE-, BENZOXAZEPINE- AND BENZOTHIAZEPINE-N-ACETIC ACID DERIVATIVES, PROCESS FOR THEIR PREPARATION AND PHARMACEUTICAL COMPOSITIONS CONTAINING THEM

BACKGROUND OF THE INVENTION

The present invention relates to novel benzazepine-, benzoxazepine- and benzothiazepine-N-acetic acid derivatives which contain an oxo group in the position α to the nitrogen atom and are substituted in position 3 by a 1-(carboxyalkyl)cyclopentylcarbonylamino radical, to salts and biolabile esters thereof, and to pharmaceutical compositions containing these compounds and processes for preparing these compounds.

SUMMARY OF THE INVENTION

It is the object of the invention to provide new benzazepine, benzoxazepine and benzothiazepine compounds with valuable pharmacological properties.

Another object of the invention is to provide new pharmaceutically active substances which can be used to treat heart failure.

It has now been found that the novel benzazepine-, benzoxazepine- and benzothiazepine-N-acetic acid derivatives which carry in position 3 an optionally esterified 1-(carboxyalkyl)cyclopentylcarbonylamino radical have valuable pharmacological properties acting on the heart and have a pronounced inhibitory effect on neutral endopeptidase (NEP) with a favorable activity profile, on the basis of which they are able to reduce the high cardiac filling pressure occurring in heart failure and thus relieve the heart and enhance diuresis.

DETAILED DESCRIPTION OF PREFERRED EMBODIMENTS

The invention therefore relates to novel compounds of the general formula I

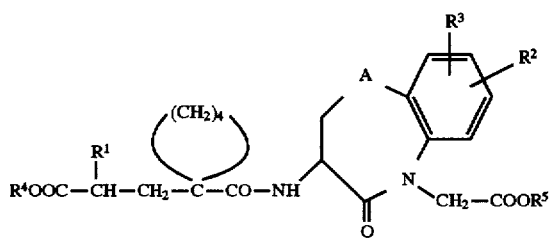

in which $R^1$ is a lower alkoxy-lower-alkyl group whose lower alkoxy radical is substituted by a lower alkoxy group, or a phenyl-lower-alkyl or phenyloxy-lower-alkyl group which can optionally be substituted in the phenyl ring by lower alkyl, lower alkoxy or halogen, or a naphthyl-lower-alkyl group, A is $CH_2$, O or S, $R^2$ is hydrogen or halogen, $R^3$ is hydrogen or halogen, $R^4$ is hydrogen or a group forming a biolabile ester, and $R^5$ is hydrogen or a group forming a biolabile ester, and the physiologically acceptable salts of the acids of formula I.

Where the substituents in the compounds of formula I are or contain lower alkyl or alkoxy groups, these can be straight-chain or branched and contain, in particular, 1 to 4, preferably 1 to 2, carbon atoms and are preferably methyl or methoxy. Where the substituents are halogen or contain halogen substituents, particularly suitable are fluorine, chlorine or bromine, preferably fluorine or chlorine.

A in the compounds of formula I can be a methylene group, oxygen or sulfur and is preferably methylene. The compounds of formula I can carry the substituents $R^2$ and $R^3$ in the phenyl ring. Both substituents $R^2$ and $R^3$, or at least one of these substituents however, are preferably hydrogen.

$R^1$ is preferably a radical containing an aromatic ring, for example an optionally substituted phenyl-lower-alkyl or phenyloxy-lower-alkyl radical in which the lower alkylene chain can contain 1 to 4, preferably 1 to 2, carbon atoms. $R^1$ is, in particular, an optionally substituted phenethyl group which can optionally be substituted one or more times by halogen, lower alkoxy or lower alkyl or is a naphthylethyl group. Where $R^1$ is a lower alkoxy-lower-alkyl group which is substituted by lower alkoxy, this is preferably a lower alkoxymethyl group in which the lower alkoxy radical contains 1 to 4, preferably 1 to 2, carbon atoms and is substituted by lower alkoxy, especially methoxy.

The compounds of formula I are optionally esterified dicarboxylic acid derivatives. Depending on the mode of administration, biolabile monoesters, especially compounds in which $R^4$ is a group forming a biolabile ester and $R^5$ is hydrogen, or dicarboxylic acids are preferred, the latter being particularly suitable for i.v. administration.

Suitable groups $R^4$ and $R^5$ forming biolabile esters include lower alkyl groups, phenyl or phenyl-lower-alkyl groups which are optionally substituted in the phenyl ring by lower alkyl or by a lower alkylene chain bonded to two adjacent carbon atoms, dioxolanylmethyl groups which are optionally substituted in the dioxolane ring by lower alkyl, or $C_2$–$C_6$-alkanoyloxymethyl groups which are optionally substituted on the oxymethyl group by lower alkyl. Where the group $R^4$ or $R^5$ forming a biolabile ester is lower alkyl, this can be a preferably unbranched alkyl group with 1 to 4, preferably 2, carbon atoms. Where the group forming a biolabile ester is an optionally substituted phenyl-lower-alkyl group, its alkylene chain can contain 1 to 3, preferably 1 carbon atoms. Where the phenyl ring is substituted by a lower alkylene chain, this can contain 3 to 4, in particular 3, carbon atoms. Particularly suitable phenyl-containing substituents $R^4$ and/or $R^5$ are phenyl, benzyl or indanyl. Where $R^4$ and/or $R^5$ are an optionally substituted alkanoyloxymethyl group, its alkanoyloxy group can contain 2 to 6, preferably 3 to 5, carbon atoms and is preferably branched and can be, for example, a pivaloyloxymethyl radical (tert-butylcarbonyloxymethyl radical).

The novel compounds of formula I and their salts according to the invention are obtained by reacting acids of the general formula II

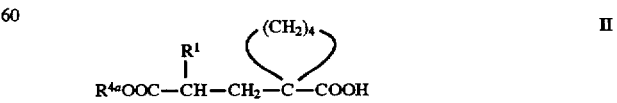

in which $R^1$ has the above meaning and $R^{4a}$ is an acid protective group, or the reactive acid derivatives thereof, in a known manner with amines of the general formula III

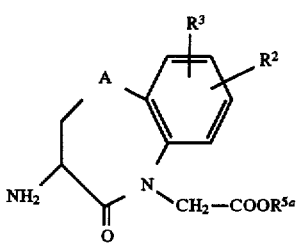

in which $R^2$, $R^3$ and A have the above meanings, and $R^{5a}$ is an acid protective group, to give amides of the general formula IV

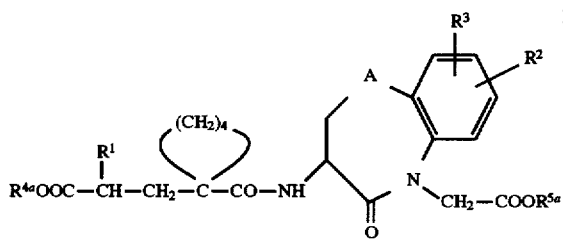

in which $R^1$, $R^2$, $R^3$, $R^{4a}$, $R^{5a}$ and A have the above meanings, and eliminating simultaneously or successively in any desired sequence the acid protective groups $R^{4a}$ and $R^{5a}$, unless they are a required group forming a biolabile ester, in the compounds of formula IV, and, if required, esterifying each unblocked acid group with an alcohol of the general formula V $$R^6\text{—OH} \qquad V$$

or a corresponding reactive derivative of the general formula Va $$R^6\text{—X} \qquad Va$$

in which $R^6$ is a group forming a biolabile ester and X is a reactive group which can be eliminated, and, if required, converting resulting acids of formula I into their physiologically acceptable salts, or converting salts of the acids of formula I into the free acids.

Suitable physiologically acceptable salts of dicarboxylic acids or monoesters of formula I include their alkali metal, alkaline earth metal or ammonium salts, for example sodium or calcium salts or salts with physiologically acceptable, pharmacologically neutral organic amines such as, for example diethylamine or tert-butylamine.

The compounds of formula I contain two asymmetric carbon atoms, namely the carbon atom which is in position 3 of the ring framework and carries the amide side chain, and the carbon atom which carries the radical $R^1$ in the amide side chain. The compounds can thus exist in several optically active stereoisomeric forms or as racemate. The present invention embraces both the racemic mixtures and the isomerically pure compounds of formula I.

The reaction of the acids of formula II with the amines of formula III to give the amides of formula IV can be carried out by conventional methods for forming amide groups by aminoacylation. Acylating agents which can be used include the acids of formula II or their reactive derivatives. Particularly suitable reactive derivatives include mixed acid anhydrides and acid halides. Thus, for example, acid chlorides or acid bromides of the acids of formula II or mixed anhydrides of the acids of formula II with organic sulfonic acids, for example lower alkanesulfonic acids such as, for example, methanesulfonic acid or aromatic sulfonic acids such as, for example, benzenesulfonic acid or benzenesulfonic acids substituted by lower alkyl or halogen, for example toluenesulfonic acids or bromobenzenesulfonic acids, can be used. The acylation can be carried out in an organic solvent which is inert under the reaction conditions, preferably at temperatures between −20° C. and room temperature. Particularly suitable solvents include halogenated hydrocarbons such as dichloromethane, or aromatic hydrocarbons such as benzene or toluene, or cyclic ethers such as tetrahydrofuran or dioxane, or mixtures of these solvents. The acylation can advantageously be carried out, especially when a mixed anhydride of the acids of formula II with a sulfonic acid is used as acylating agent, in the presence of an acid-binding reagent. Suitable acid-binding agents are bases which are soluble in the reaction mixture, especially organic bases such as tert-lower-alkylamines and pyridines such as, for example, triethylamine, tripropylamine, pyridine, 4-dimethylaminopyridine, 4-diethylaminopyridine or 4-pyrrolidinopyridine. Organic bases used in excess can also simultaneously serve as solvents.

It is possible and advantageous for mixed acid anhydrides of the acids of formula II with organic sulfonic acids to be obtained in situ by reacting the acids of formula II with an acid halide, especially the acid chloride, of the organic sulfonic acid and to be reacted directly, without isolation, further with the amine compound of formula III.

If the acids of formula II themselves are used as acylating agents, the reaction of the amino compounds of formula III with the acids of formula II can also be advantageously carried out in the presence of a coupling reagent known from peptide chemistry to be suitable for amide formation. Examples which may be particularly mentioned of coupling reagents which promote amide formation with the free acids by reacting with the acid in situ to form a reactive acid derivative, include alkylcarbodiimides, for example cycloalkylcarbodiimides such as dicyclohexylcarbodiimide or 1-ethyl-3-[3-(dimethylamino)propyl]carbodiimide, carbonyldiimidazole and N-lower-alkyl-2-halopyridinium salts, especially halides or tosylates, preferably N-methyl-2-chloropyridinium iodide (see, for example, Mukaijama in *Angewandte Chemie* 91, pages 789–812). The reaction in the presence of a coupling reagent can advantageously be carried out at temperatures from −30 to +50° C. using solvents such as halogenated hydrocarbons and/or aromatic solvents, where appropriate in the presence of an acid-binding amine.

If the protective groups $R^{4a}$ and $R^{5a}$ are not groups required in the compounds of formula I for forming a biolabile ester, they can be eliminated in a known manner from the compounds of formula IV obtained by reacting the compounds of formula II with the compounds of formula III.

The protective groups $R^{4a}$ and $R^{5a}$ may be any groups which are conventionally used for protecting acid functionalities and which can be subsequently eliminated again by known methods. Suitable acid protective groups are disclosed, for example, in McOmie, "*Protective Groups in Organic Chemistry*", Plenum Press and in Greene, "*Protective Groups in Organic Synthesis*" Wiley Interscience Publications.

Where compounds of formula I in which $R^4$ and $R^5$ are identical are to be prepared, it is advantageous to choose identical protective groups $R^{4a}$ and $R^{5a}$ in the starting compounds II and III.

Where compounds of formula I in which $R^4$ and $R^5$ have different meanings are to be prepared, it is advantageous to choose different protective groups, which can be selectively eliminated again under different conditions in a known manner, in the starting compounds II and III. Examples which may be mentioned of three protective groups which can be eliminated under different conditions include:

1. Methyl or ethyl esters which are easily cleaved under basic conditions but are considerably more stable to acidic conditions or hydrogenolysis,
2. tert-butyl esters which can easily be cleaved by acids but are considerably more stable to basic conditions or hydrogenolysis, and
3. benzyl esters which can easily be cleaved by hydrogenolysis or else under basic conditions but are considerably more stable to acidic conditions.

If, for example, dicarboxylic acid compounds of formula I in which $R^4$ and $R^5$ are both hydrogen are to be prepared, the protective groups $R^{4a}$ and $R^{5a}$ which are preferably used are protective groups which can be eliminated by acid, for example the tert-butyl group, and the tert-butyl ester compounds of formula IV obtained by reacting the compounds of formula II with the compounds of formula III are subsequently cleaved by treatment with acid. The cleavage can take place, for example, by treatment with trifluoroacetic acid as such or with a solution of trifluoroacetic acid in a halogenated hydrocarbon, for example dichloromethane, or by treatment with HCl gas in an organic solvent which is inert under the reaction conditions, for example ethyl acetate. The reaction can be carried out at temperatures between −25° C. and room temperature.

If, for example, monocarboxylic acid compounds of formula I in which $R^4$ is a group forming a biolabile ester, and $R^5$ is hydrogen, are to be prepared, it is possible to use as starting compounds of formula II, compounds in which $R^{4a}$ is already the required group forming a biolabile ester, for example the ethyl group, and as protective group $R^{5a}$ in the compounds of formula III protective groups which are cleaved under conditions under which the $R^4$—OCO group is not cleaved. If the $R^4$—OCO group is the relatively acid-stable ethyl ester group, a suitable protective group $R^{5a}$ is, for example, the tert-butyl group which can be eliminated by acid or a group which can be eliminated by hydrogenolysis, such as benzyl.

If $R^{4a}$ in the compounds of formula II is an acid-sensitive group forming a biolabile ester, it is advantageous to chose as protective group $R^{5a}$ in the compounds of formula IIIa a group which can be eliminated by hydrogenolysis, such as benzyl, and to eliminate this by hydrogenolysis from the compounds of formula IV derived from reaction of the compounds of formula II with the compounds of formula III. The hydrogenolysis can be carried out by catalytic hydrogenation in the presence of a catalyst, preferably a Pd/C catalyst, in an organic solvent which is inert under the reaction conditions, for example a lower alcohol such as ethanol or a lower alkyl ester such as ethyl acetate. The catalytic hydrogenation is advantageously carried out under a pressure of 4 to 5 bar of hydrogen at room temperature.

To prepare compounds of formula I in which $R^4$ is a group forming a biolabile ester and $R^5$ is hydrogen, however, it is also possible to choose starting compounds of formulas II and III with different protective groups $R^{4a}$ and $R^{5a}$ with different reactivities and first to eliminate the protective group $R^{4a}$, with retention of the protective group $R^{5a}$, from the compounds of formula IV obtained by reacting compounds of formula II with compounds of formula III, then to introduce into the reaction product of the general formula IV'

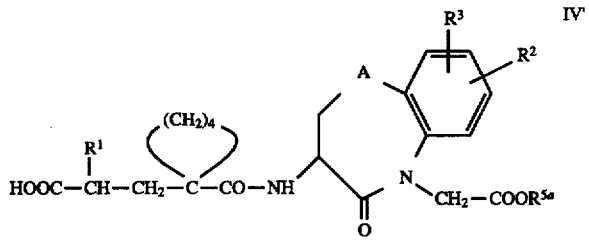

in which $R^1$, $R^2$, $R^3$, $R^{5a}$ and A have the above meanings, the required group $R^4$ forming a biolabile ester by reacting the free acid group of the compound of formula IV' with a compound of formula V or Va, and subsequently to eliminate the protective group $R^{5a}$ from the resulting compounds of formula IV.

Thus, for example, it is possible to carry out acidic elimination only of the protective group $R^{4a}$ from compounds of formula IV in which $R^{4a}$ is a protective group which can be eliminated by acid, in particular the tert-butyl group, and $R^{5a}$ is an acid-stable protective group, for example benzyl. The resulting monocarboxylic acid of formula IV' can then be esterified with an alcohol of formula V or a corresponding compound of formula Va by conventional methods for ester formation. Suitable reactive groups X which can be eliminated in the compounds of formula Va include halogens, especially chlorine or bromine, or an organic sulfonic acid radical, for example the radical of a lower-alkanesulfonic acid such as, for example, methanesulfonic acid or of aromatic sulfonic acids such as benzenesulfonic acid or benzenesulfonic acids substituted by lower alkyl or halogen such as toluenesulfonic acids. For the esterification, alcohols of formula V can be reacted, for example, with an acid of formula IV' or a reactive acid derivative of this acid in a known manner for the acylation of alcohols. The reaction can, for example, be carried out under the reaction conditions described above for reacting compounds of formula II with compounds of formula III.

It is possible in an analogous manner, by choosing appropriate different protective groups, also to prepare compounds of formula I in which $R^5$ is a group forming a biolabile ester, and $R^4$ is hydrogen or a group forming a biolabile ester and differing from $R^5$.

In the reactions described above, the asymmetric centers in the starting compounds of formulas II and III are unchanged so that, depending on the nature of the starting compounds, isomerically pure compounds of formula I or mixtures of isomers may be obtained. To prepare isomerically pure and thus optically homogeneous compounds of formula I, it is advantageous to react enantiomerically pure compounds of formula II with enantiomerically pure compounds of formula III. If an enantiomerically pure compound of formula II is reacted with a racemic compound of formula III or a racemic compound of formula II is reacted with an enantiomerically pure compound of formula III, in each case a mixture of two diastereomers is obtained and can, if required, be fractionated in a known manner. Reaction of racemic compounds of formula II with racemic compounds of formula III yields corresponding mixtures of four isomers which can, if required, be fractionated in a known manner.

The starting compounds of formula II can be obtained by known methods. For example, compounds of the general formula IIa

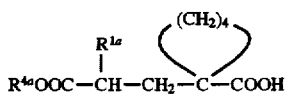

in which $R^{4a}$ has the above meaning, and $R^{1a}$ has the meaning stated for $R^1$ with the exception of a lower alkoxy-lower-alkoxymethyl radical, can be obtained by reacting acrylic acid derivatives of the general formula VI

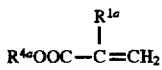

in which $R^{4a}$ and $R^{1a}$ have the above meanings, with cyclopentanecarboxylic acid of formula VII

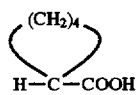

The reaction can be carried out in a known manner under the conditions of a Michael addition in an organic solvent which is inert under the reaction conditions by reacting the cyclopentanecarboxylic acid with a strong base which is able to form the dianion of cyclopentanecarboxylic acid, and subsequently reacting with the acrylic ester derivative of formula VI. Suitable solvents include ethers, especially cyclic ethers such as, for example, tetrahydrofuran. Suitable strong bases include non-nucleophilic organic alkali metal amides such as, for example, lithium diisopropylamide. It is advantageous to react the cyclopentanecarboxylic acid in tetrahydrofuran with two equivalents of lithium diisopropylamide, and subsequently to react the reaction mixture with the compound of formula VI. The reaction temperature can be between −70° and 0° C.

Compounds of the general formula IIb

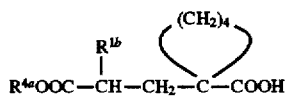

in which $R^{4a}$ has the above meaning, and $R^{1b}$ is a lower alkoxy-lower-alkoxymethyl radical, can be obtained by reacting halo carboxylic esters of the general formula VIII $$R^{4a}OOC-CH_2-CH_2-Y \qquad \text{VIII}$$

in which $R^{4a}$ has the above meaning, and Y is halogen, with cyclopentanecarboxylic acid of formula VII, and reacting the resulting reaction product of the general formula IX

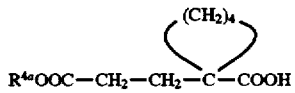

in which $R^{4a}$ has the above meaning, with compounds of the general formula Xb $$R^{1b}-X \qquad \text{Xb}$$

in which $R^{1b}$ and X have the above meanings. The reaction of the halo carboxylic esters of formula VIII with the cyclopentanecarboxylic acid of formula VII can be carried out in a known manner in a solvent which is inert under the reaction conditions in the presence of a strong base which is able to form the dianion of cyclopentanecarboxylic acid. For example, the reaction can be carried out under the conditions stated for the reaction of cyclopentanecarboxylic acid with compounds of formula VI. The subsequent reaction of the acids of formula IX with compounds of formula Xb can be carried out in a known manner under conditions suitable for the α-alkylation of carboxylic esters in an organic solvent which is inert under the reaction conditions in the presence of a strong base. Preferred compounds of formula Xb include those in which X is chlorine or bromine. Suitable solvents include ethers, especially cyclic ethers such as tetrahydrofuran or dioxane. It is possible to use as strong base alkali metal hydrides or amides, for example lithium diisopropylamide.

The compounds of formula II have an asymmetric center on the carbon atom carrying the radical $R^1$ and are obtained in the form of their racemates from the synthesis. The optically active compounds can be obtained from the racemic mixtures in a known manner, for example by chromatographic separation on chiral separating materials or by reaction with suitable optically active bases, for example α-methylbenzylamine or pseudoephedrine, and subsequent fractionation into their optical antipodes by fractional crystallicrystallization of the resulting salts.

Acrylic ester derivatives of formula VI can be obtained in a known manner by reacting (dilower-alkylphosphono) acetic ester derivatives of the general formula XI

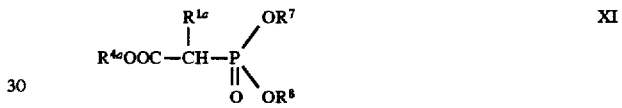

in which $R^{4a}$ and $R^{1a}$ have the above meanings, and $R^7$ and $R^8$ are each lower alkyl, preferably methyl or ethyl, with formaldehyde under basic conditions in an organic solvent which is inert under the reaction conditions. For example, compounds of formula XI can be reacted with paraformaldehyde in an ether, preferably a cyclic ether such as tetrahydrofuran, in the presence of a base, preferably a non-nucleophilic alkali metal alcoholate such as potassium tert-butoxide, at temperatures between −20° and +30° C.

Compounds of formula XI can be obtained in a known manner by reacting phosphonoacetic acid derivatives of the general formula XII

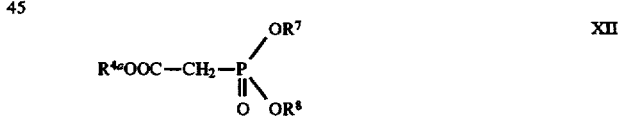

in which $R^{4a}$, $R^7$ and $R^8$ have the above meanings, with compounds of formula Xa $$R^{1a}-X \qquad \text{Xa}$$

in which $R^a$ and X have the above meanings. The reaction can be carried out under customary conditions for alkylation in a polar aprotic organic solvent which is inert under the reaction conditions in the presence of a base at temperatures between 0° and 80° C. Preferred compounds of formula Xa include those in which X is halogen, especially bromine or iodine, or tosylate. Examples of suitable solvents include amides, such as dimethylformamide, or ethers. Suitable bases include non-nucleophilic alkali metal alcoholates such as, for example, potassium tert-butoxide.

Compounds of formula VI can also be obtained by treating malonic acid derivatives of the general formula XIII $$\underset{\text{R}^{4a}\text{OOC—CH—COOH}}{\overset{\text{R}^{1a}}{|}} \qquad \text{XIII}$$

in which $R^{4a}$ and $R^{1a}$ have the above meanings, in a known manner with formaldehyde under basic conditions. Thus, for example, malonic acid derivatives of formula XIII can be reacted with an aqueous formaldehyde solution in the presence of a secondary organic amine, especially piperidine, at temperatures between 0° and 30° C., preferably at temperatures below room temperature. The malonic acid derivatives of formula XIII can also be reacted with paraformaldehyde in pyridine at temperatures between 40° and 60° C.

The malonic monoesters of formula XIII can be obtained by reacting malonic diesters of the general formula XIV $$\text{R}^{4a}\text{OOC—CH}_2\text{—COOR}^9 \qquad \text{XIV}$$

in which $R^{4a}$ has the above meaning, and $R^9$ is lower alkyl, especially methyl or benzyl, with compounds of formula Xa, and converting the resulting malonic diester derivatives of the general formula XV $$\underset{\text{R}^{4a}\text{OOC—CH—COOR}^9}{\overset{\text{R}^{1a}}{|}} \qquad \text{XV}$$

in which $R^{1a}$, $R^{4a}$ and $R^9$ have the above meanings, by partial hydrolysis into the corresponding malonic monoester derivatives of formula XIII.

The introduction of the radical $R^{1a}$ into the malonic diesters of formula XIV can be carried out in a known manner by reacting the esters of formula XIV with a compound of formula Xa in a polar aprotic organic solvent, preferably dimethylformamide, in the presence of a base, for example a non-nucleophilic alkali metal alcoholate such as potassium tert-butoxide at temperatures between 0° C. and 80° C. The reaction can, for example, be carried out under the conditions described above for the reaction of compounds of formula XI with compounds of formula Xa.

The resulting substituted malonic diesters of formula XV can be converted into the corresponding malonic monoesters of formula XIII by eliminating the radical $R^9$ in a known manner. Where the protective group $R^{4a}$ and the radical $R^9$ are different radicals with different reactivities, it is advantageous to choose for the elimination of the radical $R^9$ conditions under which the radical $R^{4a}$ is not attacked. Where $R^9$ is benzyl, the elimination can take place in a known manner by hydrogenolysis. Lower alkyl esters $R^9$ are eliminated by hydrolysis in a known manner, under acidic or alkaline conditions depending on the nature of the alkyl radical. $R^9$ is preferably ethyl, which can be eliminated by alkaline hydrolysis. It is possible for this purpose to treat the alkyl esters of formula XV in a lower alcohol or a mixture of a lower alcohol with water with an alkali metal hydroxide, for example potassium hydroxide. Where the radicals $R^{4a}$ and $R^9$ are identical, in this case the amount of alkali metal hydroxide is kept so low that only partial hydrolysis occurs.

Compounds of formula III can be obtained in a known manner by reacting compounds of the general formula XVI

XVI in which $R^2$, $R^3$ and A have the above meanings, and the $R^{10}R^{11}N$ group is an amino group protected by an amino protective group, with compounds of the general formula XVII $$\text{X—CH}_2\text{—COOR}^{5a} \qquad \text{XVII}$$

in which $R^{5a}$ and X have the above meanings, and liberating the free amino group from the $R^{10}R^{11}N$ group in the resulting reaction product of the general formula XVIII

XVIII in which $R^2$, $R^3$, $R^{5a}$, A and the $R^{10}R^{11}N$ group have the above meanings. Reaction of compounds of formula XVI with compounds of formula XVII can be carried out by conventional methods for the alkylation of amides. Preferred compounds of formula XVII include those in which X is halogen, preferably bromine or iodine. The reaction can be carried out in a polar aprotic organic solvent, for example dimethylformamide or a cyclic ether such as tetrahydrofuran and in the presence of a base. Suitable bases include non-nucleophilic bases such as, for example, potassium tert-butoxide. If required, the reaction can also be carried out in the presence of an alkali metal hydroxide, for example potassium hydroxide, in a two-phase system in the presence of a phase-transfer catalyst, for example a tetra-lower-alkylammonium halide such as tetrabutylammonium bromide.

The amino group in the resulting compounds of formula XVIII can subsequently be liberated by removing the protective group in a known manner. Protective groups which are known for protecting amino groups and can easily be removed, for example the protective groups known from peptide chemistry, can be used to protect the amino group. Examples of suitable protective groups are disclosed in E. McComie "Protective groups in organic chemistry" Plenum Press 1971. Examples of suitable protective groups include the phthalimide group, the tert-butoxycarbonyl group, or the benzyloxycarbonyl group. It is necessary in each case to choose, depending on the meaning of $R^{5a}$, protective groups which can subsequently be eliminated under conditions under which the $R^{5a}$ group is not attacked. An example of a suitable protective group which can be eliminated in basic medium is the phthalimide group which can be eliminated by treatment with ethanolamine or with hydrazine at elevated temperatures, for example temperatures between 70° and 90° C. The phthalimide group is suitable, for example, as protective group for compounds in which A is sulfur. An example of a suitable protective group which can be eliminated by acid is the tert-butoxycarbonyl group which can be removed by treatment with acid, for example by treatment with trifluoroacetic acid or with hydrogen chloride gas in ethyl acetate. The tert-butoxycarbonyl group is suitable, for example, as protective group for compounds in which A is oxygen. An example of a suitable protective group which can be eliminated by hydrogenolysis is the benzyloxycarbonyl group which can be eliminated by hydrogenation with hydrogen in the presence of a palladium/charcoal catalyst.

The compounds of formula III contain an asymmetric center at the carbon atom carrying the amino group. Where the starting compounds of formula XVI are optically pure, optically pure compounds of formula III are obtained. This particularly applies to those compounds in which A is oxygen or sulfur. Where the starting compounds of formula XVI are racemic, racemic compounds of formula III are also obtained. This is generally the case with compounds in which A is a methylene group. Racemic mixtures of compounds of formula III can be fractionated into their optical isomers in a known manner, for example by chromatographic separation on chiral separating materials or by reaction with suitable optically active acids, for example tartaric acid, and subsequent fractionation of the optical antipodes by fractional crystallization of the resulting salts. To increase the yield of the desired optical isomer it is possible in the reaction with suitable optically active acids to start up, at the same time as or after the substantial precipitation of the salt of one isomer with the optically active acid in the reaction mixture, a reracemization of the isomer remaining in solution by adding a, preferably aromatic, aldehyde such as, for example, benzaldehyde. In this case, the racemization at the asymmetric center is brought about by imine formation with the aldehyde.

The compounds of formula XVI can be obtained in a known manner. For example, compounds of the general formula XVIa

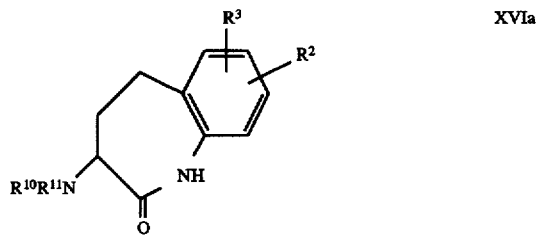

in which $R^2$, $R^3$ and the $R^{10}R^{11}N$ group have the above meanings, can be obtained by replacing the halogen Y in compounds of the general formula XIX

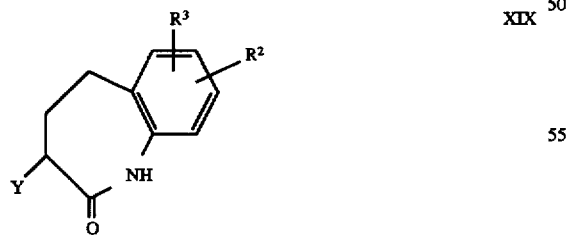

in which $R^2$, $R^3$ and Y have the above meanings by the $R^{10}R^{11}N$ group in a known manner. For example, a compound of formula XIX can be reacted with an alkali metal salt of an amide $R^{10}R^{11}NH$, preferably potassium phthalimide. The reaction can be carried out in an aprotic organic solvent which is inert under the reaction conditions, preferably dimethylformamide, at temperatures between 40° and 80° C.

Compounds of formula XIX can be obtained in a known manner by Beckmann rearrangement of oxime compounds of the general formula XX

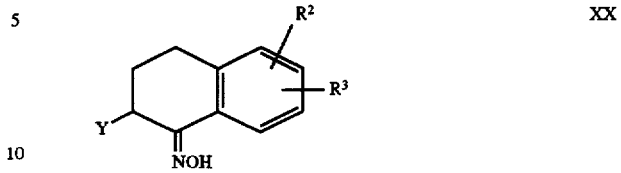

in which $R^2$, $R^3$ and Y have the above meanings, by treating compounds of formula XX with an acid under the conditions of a Beckmann rearrangement. Rearrangement of compounds of formula XX to compounds of formula XIX is advantageously carried out by treatment with polyphosphoric acid at temperatures between 60° and 90° C.

Oximes of formula XX can be obtained starting from cyclic ketones of the general formula XXI

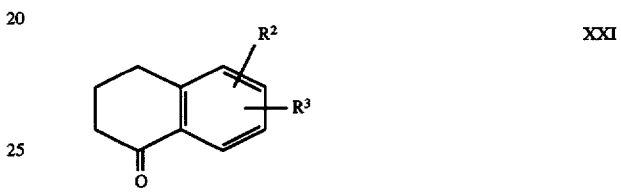

in which $R^2$ and $R^3$ have the above meanings, by initially treating the ketones of formula XXI with halogen to introduce the radical Y, and subsequently reacting the resulting halogenated ketones with hydroxylamine. The α-halogenation of the ketone and the subsequent oxime formation can advantageously be carried out in a one-pot process, in which case the ketone of formula XXI is initially treated with the halogen in an inert organic solvent, for example a lower alcohol such as methanol, and subsequently hydroxylamine is added to the reaction mixture. The hydroxylamine is advantageously used in the form of a hydroxylamine salt, for example the hydrochloride, and some water is added to the reaction mixture. The process can be carried out at temperatures between 0° and 40° C., preferably at room temperature.

Compounds of the general formula XVIb

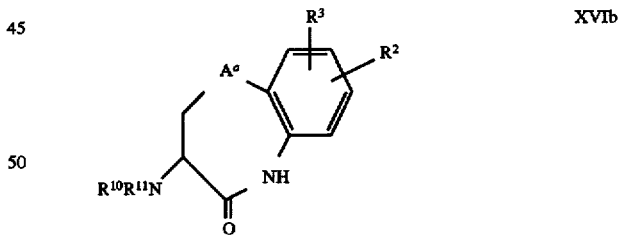

in which $R^2$, $R^3$ and the $R^{10}R^{11}N$ group have the above meanings, and $A^a$ is oxygen or sulfur, can be obtained in a known manner by cyclization of aromatic amino acid compounds of the general formula XXII

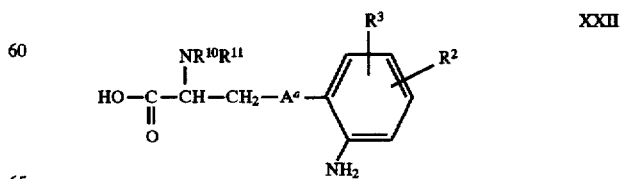

in which $R^2$, $R^3$, $A^a$ and the $R^{10}R^{11}N$ group have the above meanings. The cyclization of the compounds of formula XXII takes place with elimination of water and can be carried out by conventional methods of lactam formation. Thus, the cyclization can, for example, be carried out in the presence of a coupling reagent which activates the acid group and is known from peptide chemistry for amide formation, for example a carbodiimide, in a polar organic solvent which is inert under the reaction conditions, for example dimethylformamide. The reaction can be carried out, for example, under the conditions described for the reaction of compounds of formula II with compounds of formula III. It is also possible to use diethylphosphoryl cyanide as agent to activate the acid group, and to carry out the reaction in the presence of an organic base, for example a tri-lower-alkylamine such as triethylamine.

Compounds of the general formula XXII can be obtained in a known manner by reducing corresponding nitro compounds of the general formula XXIII

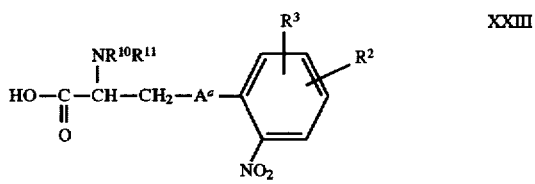

in which $R^2$, $R^3$, $A^a$ and the $R^{10}R^{11}N$ group have the above meanings. The reduction of the nitro group can be carried out by known methods for reducing nitrobenzene compounds to aniline compounds, for example by catalytic hydrogenation in the presence of a palladium/charcoal catalyst. The reduction can also be carried out using other reducing agents which generate hydrogen in situ, for example metallic iron/hydrochloric acid or metallic zinc/hydrochloric acid.

Compounds of formula XXIII can be obtained in a known manner by reacting o-fluoronitrobenzene compounds of the general formula XXIV

in which $R^2$ and $R^3$ have the above meanings, with acids of the general formula XXV

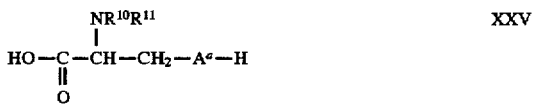

in which $A^a$ and the $R^{10}R^{11}N$ group have the above meanings. The compounds of formula XXV are serine and cysteine derivatives whose amino group is protected. The reaction takes place in an organic solvent which is inert under the reaction conditions in the presence of a base. The reaction of the fluoronitrobenzenes with the strongly nucleophilic cysteine derivative can be carried out in a lower alcohol or an alcohol/water mixture in the presence of a weak base such as sodium bicarbonate. For the reaction with the comparatively weaker nucleophilic serine derivative, it is advantageous to use a strong base, for example an alkali metal hydride, in a polar organic solvent such as dimethylformamide.

It is possible, after formation of the compounds of formula XXIII, optionally to replace the amino protective group originally present in the compounds of formula XXV in a known manner with another amino protective group which differs better in its reactivity from the radical $R^{5a}$ and which thus is more suitable for further processing of the compounds of formula XXIII.

The compounds of formula I and their pharmacologically acceptable salts are distinguished by interesting pharmacological properties. In particular, the substances exert an inhibitory effect on neutral endopeptidase (NEP). NEP is an enzyme which brings about the degradation of endogenous natriuretic peptides, for example atrial natriuretic peptide (ANP). Due to their inhibitory effect on NEP activity, the substances are able to improve the biological activity and lifetime of the natriuretic peptides which can be attacked by NEP, especially ANP, and are therefore suitable for the treatment of pathological states which are favorably influenced by the action of such hormones, especially heart failure.

In cases of heart failure, the pathologically reduced cardiac output of the heart results in a reflex increase in the peripheral resistance and thus in a congestion of the blood in the pulmonary circulation and the heart itself. The consequence is a high cardiac filling pressure which causes stretching of the chamber walls in the atria and the ventricles. In these circumstances, the heart functions like an endocrine organ, that is to say it is able to secrete ANP, which has pronounced vasodilating and diuretic/natriuretic activities, into the bloodstream. ANP acts to reduce the elevated cardiac filling pressure. This takes place by diuresis/natriuresis (reduction in the circulating blood volume) and by reducing the peripheral resistance (decrease in preload and afterload). The heart-relieving action of ANP is regarded as an endogenous cardioprotective mechanism. The action of ANP is, however, of only short duration because the hormone is rapidly cleaved by NEP.

Because of their NEP-inhibiting properties, the compounds according to the invention are able to improve the cardioprotective mechanism of action of ANP and, in particular, display great efficacy in enhancing diuretic/natriuretic activities.

The compounds according to the invention are distinguished by a favorable activity profile with good tolerability and, moreover, display substantial selectivity of the NEP-inhibitory action and additionally reveal slight inhibitory effects on endothelin-converting enzyme (ECE). In advanced stages of heart failure there are reflex elevations in the blood levels of angiotensin II, endothelin and catecholamines and thus a further increase in the peripheral resistance and the cardiac filling pressure, resulting in hypertrophy and dilatation of the myocardium. The additional ECE-inhibitory properties are able in this case to enhance the peripheral resistance-reducing effect of the substances according to the invention.

The NEP- and ECE-inhibitory and diuresis/natriuresis-enhancing properties of the substances have been demonstrated in standard pharmacological in vitro and in vivo test methods.

Description of the pharmacological investigation methods:
1. Determination of the minimum toxic dose Male mice weighing 20–25 g received oral administrations of maximum doses of 300 mg/kg of the test substance. The animals were carefully observed for signs of toxicity for 3 hours. In addition, all signs and deaths over a period of 72 hours after administration were recorded. Accompanying signs were likewise observed and recorded. If death or signs of severe toxicity were observed, further mice were given increasingly lower doses until signs of toxicity no longer appeared. The lowest dose which caused death or signs of severe toxicity is indicated in following Table A as the minimum toxic dose. The example numbers listed in Table A refer to the following preparation examples.

TABLE A

| Test substance Example No. | Minimum toxic dose mg/kg mouse, oral |
|---|---|
| 6 | >300 |
| 24 | >300 |
| 27 | >300 |
| 37 | >300 |

2. In vitro investigation of the NEP-inhibitory effect of the substances and determination of the affinity of the substance molecules for the enzyme molecule. To demonstrate the inhibitory effect of the substances according to the invention on neutral endopeptidase (NEP), the inhibitory effect of the substances on the hydrolyric degradation of methionine enkephalin (met-enkephalin), occurring due to the enzymatic activity of NEP, was investigated in a standard in vitro test. The $K_i$ (inhibitor constant) of each substance was determined as a measure of its inhibitory activity. The $K_i$ of a test substance with enzyme-inhibiting activity is the dissociation constant for the enzyme/test substance complex or the (enzyme/substrate)—test substance complex and has units of concentration.

Test procedure.

To carry out the test, respective 100 μl samples of various incubation solutions containing 10 ng of purified NEP (E.C.3.4.24.11) and in each case different amounts of test substance and of substrate (met-enkephalin) and 50 mM tris buffer (=tris(hydroxymethyl)aminomethane/HCl, pH 7.4) were prepared.

For each test substance, 24 different incubation solutions were prepared with 3 different test substance concentrations respectively combined with met-enkephalin contents of 2, 5, 7, 10, 12, 15, 40 and 100 μm.

In each test, two types of control incubation solutions were also processed, on the one hand enzyme controls which contain no test substance, and on the other hand substrate controls which contain neither enzyme nor test substance.

The incubation solutions were incubated in a shaking water bath at 37° C. for 45 minutes. The enzyme reaction was started after 15 minutes by adding the substrate (metenkephalin) and was stopped at the end of the incubation time by heating at 95° C. for 5 minutes. The stopped incubation solution was then centrifuged at 12,000×g for 3 minutes, and the concentrations of unreacted substrate and of hydrolysis products formed by the enzymatic reaction were determined in the supernatant. For this purpose, samples of each of the respective supernatants were fractionated by HPLC (high-pressure liquid chromatography) on hydrophobized silica gel, and the products of the enzymatic reaction and unreacted substrate were determined by photometry at a wavelength of 205 nm. The HPLC separation was carried out using a column (4.6×250 mm) which contains Encapharm™ 100 RP18 having an average particle size of 5 μm as reversed phase separation material. The solvent flow rate was 1.4 ml/min, and the column was warmed to 40° C. Mobile phase A was 5 mM $H_3PO_4$, pH 2.5, and mobile phase B was acetonitrile +1% 5 mM $H_3PO_4$, pH 2.5.

The $K_i$ for each test substance was calculated in a known manner from the concentrations of hydrolysis products and unreacted substrate measured in the various samples. The following Table B shows the $K_i$ values found for the test substances. The example numbers indicated in Table B refer to the following preparation examples.

TABLE B

| Test substance Example No. | $K_i$ in nM |
|---|---|
| 6 | 0.67 |
| 8 | 0.40 |
| 11 | 2.55 |
| 13 | 0.76 |
| 22 | 2.15 |
| 24 | 1.00 |
| 26 | 1.22 |
| 29 | 1.08 |

3. In vitro investigations of the ECE-inhibitory effect of the substances.

To demonstrate the inhibitory effect of the substances according to the invention on endothelin-converting enzyme (ECE), the inhibitory effect of the substances on the hydrolyric degradation, occurring due to the enzymatic activity of ECE, of big endothelin 1 (bigET-1) was investigated in a standard in vitro test. The $IC_{50}$ of the substances was determined as a measure of their inhibitory activity. The $IC_{50}$ of a test substance with enzyme-inhibiting activity is the concentration of the test substance at which 50% of the enzymatic activity of ECE is inhibited.

Preparation of the ECE-containing endothelial cell membrane fraction.

Egg cells from the Chinese hamster (Chinese hamster ovary cells, hereinafter CHO cells) in which there was recombinant expression of human ECE [see Schmidt et al., Federation of European Biochemical Societies Letters 356 238–43 (1994)] were lysed, and the cell membranes were removed by centrifugation at 10,000×g for 10 min. The cell membranes were washed by resuspension and repeated centrifugation three times. The ECE-containing cell membrane fraction was resuspended in 100 mM tris/HCl buffer (tris(hydroxymethyl)aminomethane/HCl, pH 7.0, containing 250 mM NaCl) and stored frozen at −70° C. before the enzyme test.

Test procedure.

To carry out the test, respective 100 μl samples of various incubation solutions each containing 5 μg protein from an ECE-containing preparation of endothelial cell membranes and different amounts of test substance and 24 μM substrate (synthetic peptide: $H_2$N-Asp-Ile-Ala-Trp-Phe-Asn-Thr-Pro-Glu-His-Val-Val-Pro-Tyr-Gly-Leu-Gly-COOH) (SEQ ID NO:1) and 100 mM tris buffer (tris(hydroxymethyl) aminomethane/HCl, pH 7.0, containing 250 mM sodium chloride) were prepared. In addition, each incubation solution contained 100 μM thiorphan, 10 μM captopril, 1 mM phenylsulfonyl fluoride, 100 μM pepstatin A (protease inhibitor), and 100μM amastatin (protease inhibitor).

For each test substance, six different incubation solutions were prepared in each case with three different test substance concentrations respectively as duplicate determinations. In each test, a control which contained no enzyme was also processed.

The incubation solutions were preincubated at 37° C. for 15 min before the substrate was added. The enzyme reaction was started by adding the substrate. The enzyme reaction lasted for 60 min, was carried out 37° C. and was stopped by heating the incubation solution at 95° C. for 5 min. The hydrolysis products H2N-Asp-Ile-Ala-Trp-COOH (SEQ ID NO:2) and $H_2$N-Phe-Asn-Thr-Pro-Glu-His-Val-Val-Pro-Tyr-Gly-Leu-Gly-COOH (SEQ ID NO:3) formed from the substrate by the enzymatic reaction were determined with the aid of high-pressure liquid chromatography (HPLC).

The HPLC determination was carried out as described above in the case of the in vitro investigation of the NEP-inhibitory effect. The $IC_{50}$ was calculated for each test substance in a known manner from the concentrations of hydrolysis products measured in the various samples. The following Table C shows the $IC_{50}$ values found for the test substances.

TABLE C

| Test substance Example No. | $IC_{50}$ in μM |
|---|---|
| 39 | 0.52 |
| 8 | 1.29 |
| 38 | 2.20 |

4. In vivo determination of the effect of the substances on diuresis/natriuresis in volume-loaded rats.

The in vivo activity was investigated in volume-loaded rats. In this experiment a high cardiac filling pressure was caused by infusion of isotonic sodium chloride solution, which results in ANP release and thus diuresis/natriuresis.

Test procedure:

The tests are carried out with male Wistar rats having a body weight of 200–400 g. Under neuroleptanalgesia (fentanyl; Hypnorm™, manufactured by Janssen), a catheter was placed in the right femoral vein for the baseline infusion and the volume loading with isotonic sodium chloride solution. After the abdominal cavity had been opened, a second catheter was inserted into the bladder, and the urethra was tied off so that it was possible to measure the urine volume, natriuresis and kaliuresis.

The abdominal cavity was closed again and the animals received a continuous infusion with sodium chloride solution (0.5 ml/100 g body weight) throughout the 2 hours of the test. After an equilibration period of 30 minutes, in a preliminary phase before the test substance was given, urine samples were collected three times over a period of 10 minutes in each case. These preliminary values ("predrug" values) were determined in order to check that there was a continuous flow of urine in the test animals.

The solutions containing test substances were then administered intravenously (bolus injection into the femoral vein) or orally (by gavage) to groups of 10 rats each. With both modes of administration, in each case one control group of animals received only placebo solutions which contained no active substance. 5 Minutes after i.v. administration or 120 minutes after oral administration of the substances, the rats were loaded with an increased volume of sodium chloride solution i.v. (2 ml/100 g body weight in 2 minutes) and the urine was collected over a period of 60 min. The amounts of urine produced in this period were determined, and the sodium and potassium contents therein were measured. The increase in excretion which took place under volume loading by comparison with the preliminary values was deduced from the resulting amounts of urine.

The following Table D shows the increases in the excretion of urine occurring under volume loading after administration of test substance as a percentage based on the increases in the excretion of urine occurring under volume loading after placebo administration. Furthermore, the amounts of sodium and potassium excreted under volume loading after administration of test substance are also indicated as a percentage of the amounts of sodium and potassium excreted under volume loading after placebo administration.

TABLE D

| Test substance Example No. | Mode of administration Dose in mg/kg | Increase in the excretion of urine under volume loading after administration of test substance as % based on the increase in the excretion of urine under volume loading after placebo administration | Na and K excretion under volume loading, amount excreted after administration of test substance as % of the amount excreted after placebo administration | |
|---|---|---|---|---|
| | | | Na | K |
| 8 | 0.1 i.v. | 123.5% | 160.9% | 80.8% |
| 8 | 1.0 i.v. | 153.7% | 230.4% | 121.8% |
| 4 | 15 p.o. | 196.5% | n* | n* |
| 4 | 51 p.o. | 271% | n* | n* | n* = not determined

The foregoing test results show that the compounds of formula I have a high affinity for NEP and contribute, by inhibiting this ANP-degrading enzyme, to an increase in the ANP level in the blood and thus dose-dependently increase the diuretic/natriuretic effects induced by ANP while causing a negligible loss of potassium.

Because of their effect described above, the compounds of formula I are suitable as medicaments for larger mammals, especially humans, for treating heart failure and for promoting diuresis/natriuresis, especially in patients suffering from heart failure. For this purpose, dicarboxylic acids of formula I and their salts are advantageously used in medicinal forms which can be administered parenterally, especially i.v., and mono- or diesters of formula I are advantageously used in medicinal forms which can be administered orally. The doses to be used may vary individually and, of course, vary with the nature of the condition to be treated, the substance used and the mode of administration. For example, parenteral formulations generally contain less active substance than oral products. However, medicinal forms with an active substance content of from 1 to 200 mg per individual dose are generally suitable for administrations to larger mammals, especially humans.

As medicines, the compounds of formula I can be admixed with customary pharmaceutical ancillary substances in pharmaceutical compositions such as, for example, tablets, capsules, suppositories or solutions. These pharmaceutical compositions can be produced by known methods using conventional solid or liquid vehicles such as, for example, lactose, starch or talc or liquid paraffins and/or using customary pharmaceutical ancillary substances, for example tablet disintegrants, solubilizers or preservatives.

The following examples are intended to illustrate the invention in further detail without restricting its scope.

The structures of the novel compounds were confirmed by spectroscopic investigations, in particular by analysis of the NMR, mass, IR and/or UV spectra and, where appropriate, determining the optical rotations.

EXAMPLE 1

Tert-butyl 3-{1-[2'-(ethoxycarbonyl)-4'-phenylbutyl]cyclopentane-1'-carbonylamino}-2,3,4,5-tetrahydro-2-oxo-1H-1-benzazepine-1-acetate.

A) 123.4 g of potassium tert-butoxide were added in portions to a solution of 160.1 g of diethyl malonate in one liter of dimethylformamide at a temperature of 15° C. The reaction mixture was stirred for 30 min and then, at room temperature, a solution of 207.7 g of phenethyl bromide in 200 ml of dimethylformamide was added dropwise. The reaction mixture was subsequently heated at 60° C for one hour and left to cool again.

The dimethylformamide was evaporated under reduced pressure, and the residue was taken up in a mixture of methyl tert-butyl ether and water. The organic phase was separated, washed with water, dried over sodium sulfate and evaporated. The crude product remaining as an oily residue was purified by distillation under reduced pressure. 202.5 g of ethyl 2-ethoxycarbonyl-4-phenylbutanoate were obtained, boiling point at 1.5 Torr=148°–153° C.

B) A solution of 6.17 g of potassium hydroxide in 76 ml of water was added to a solution of 23.6 g of the diester product obtained above in 285 ml of ethanol while cooling in ice. The reaction mixture was stirred at room temperature for several hours. The ethanol was subsequently evaporated off under reduced pressure, and the residue was taken up in a mixture of methyl tert-butyl ether and water. The organic phase was separated and discarded, and the aqueous phase was acidified with dilute aqueous hydrochloric acid while cooling in ice and subsequently extracted several times with methyl tert-butyl ether. The combined methyl tert-butyl ether phases were washed with water, dried over sodium sulfate and evaporated under reduced pressure. 20.2 g of crude oily ethyl 2-carboxy-4-phenylbutanoate were obtained and were further processed without further purification.

C) 11 ml of 35% strength aqueous formaldehyde solution and 9.23 ml of piperidine were successively added to 20.2 g of the product obtained above while cooling in ice. The reaction mixture was stirred at room temperature for several hours, then diluted with methyl tert-butyl ether, washed with aqueous potassium bisulfate and with water, dried over sodium sulfate and evaporated. The residue was dried under reduced pressure. 14.8 g of ethyl α-(2-phenylethyl)acrylate were obtained.

D) Under a nitrogen atmosphere, 25.2 ml of diisopropylamine were dissolved in 150 ml of absolute tetrahydrofuran and cooled to −35° C. 100 ml of a 1.6 normal solution of butyllithium in n-hexane were added dropwise to the solution. The reaction mixture was then stirred at 0° C. for 30 minutes and subsequently a solution of 8.1 ml of cyclopentanecarboxylic acid in 20 ml of absolute tetrahydrofuran was added dropwise. The reaction mixture was stirred at 0° C. for 2 hours. Then a solution of 16.8 g of the acrylic ester obtained under C) in 20 ml of absolute tetrahydrofuran was added dropwise, and the reaction mixture was allowed to stand at 0° C. for 2 hours and subsequently at −15° C. for several hours. For working up, the reaction mixture was acidified with 10% strength aqueous hydrochloric acid solution and extracted with n-hexane. The organic phase was washed seven times with half-saturated aqueous sodium bicarbonate solution and once with water, dried over sodium sulfate and evaporated under reduced pressure. The crude product obtained as residue was purified by flash chromatography on silica gel using n-hexane/ethyl acetate (8:2). 19.6 g of pure 1-[2'-(ethoxycarbonyl)-4'-phenylbutyl]cyclopentane-1-carboxylic acid were obtained with a melting point of 68° to 69° C.

E) 108.3 g of bromine were slowly added dropwise to a solution of 100 g of α-tetralone in 820 ml of methanol while cooling in ice. The reaction mixture was subsequently stirred at room temperature for 30 minutes and then first 122.4 g of hydroxylamine hydrochloride and subsequently 110 ml of water were added at room temperature. The mixture was stirred at room temperature for 3 days. Then a further 493 ml of water were added, whereupon a white precipitate separated out after 1 hour. The reaction mixture was stirred for a further 3 days and then cooled to 5° C. The precipitate was filtered out with suction, washed with water and dried under reduced pressure at 40° C. 136.7 g of 2-bromo-3,4-dihydronaphthalen-1(2H)-one oxime with a melting point of 130° to 132° C. were obtained.

F) 79.5 g of the oxime obtained above were added in portions to 452 g of polyphosphoric acid heated to 80° C., and the reaction mixture was stirred at 80° C. for 18 hours. Subsequently the mixture was cautiously diluted with 710 ml of water and stirred at room temperature for 2 hours. The resulting precipitate was filtered out with suction, washed with water, aqueous sodium bicarbonate solution, again with water and then finally with methyl tert-butyl ether and dried over potassium hydroxide at a temperature of 60° C. 66.6 g of 3-bromo-4,5-dihydro-1H-1-benzazepin-2(3H)-one with a melting point of 168° to 170° C. were obtained.

G) 80 g of the product obtained above were suspended in 140 ml of dimethylformamide. A solution of 72.6 g of potassium phthalimide in 205 ml of dimethylformamide was added to the suspension, which was subsequently stirred at 60° C. for 16 hours. For working up, the mixture was cooled to room temperature and 800 ml of water were slowly added dropwise, and the mixture was stirred while cooling in ice for 2 hours. The resulting mass of crystals was filtered out with suction and washed first with a water/dimethylformamide mixture and then with methyl tert-butyl ether and subsequently dried under reduced pressure at 60° C. for 2 days. 73.3 g of 4,5-dihydro-3-phthalimido-1H-1-benzazepin-2(3H)-one with a melting range from 185 to 195° C. were obtained.

H) A solution of 12.3 g of potassium tert-butoxide in 40 ml of dimethylformamide was added to a suspension of 27 g of the product obtained above in 90 ml of dimethylformamide while cooling in ice. After stirring while cooling in ice for 30 minutes, 20.7 g of tert-butyl bromoacetate were added dropwise over the course of one hour at 0° to 5° C. The mixture was stirred at 0° C. for one hour. The reaction mixture was then warmed to 40° C., and 164 ml of water were added dropwise over the course of 3 hours and the mixture was then stirred at 30° C. for one hour.

The aqueous solution was then decanted off from the precipitate which had formed and the remaining solid residue was crystallized from methyl tert-butyl ether. The crystals which formed were filtered out with suction, washed with water and methyl tert-butyl ether and dried under reduced pressure at 60° C. 26.3 g of tert-butyl 2,3,4,5-tetrahydro-2-oxo-3-phthalimido-1H-1-benzazepine-1-acetate with a melting point of 194°–197° C. were obtained.

E) 7 g of the ester obtained above were added over the course of 5 minutes to 13.8 ml of ethanolamine heated to 80° C. A clear solution had formed after 5 minutes, and this was cooled to room temperature and diluted with 105 ml of toluene. The solution was extracted by shaking with 140 ml of 5% strength aqueous sodium chloride solution, and the organic phase was separated, dried over sodium sulfate and evaporated. The residue was crystallized from methyl tert-butyl ether. 4.0 g of tert-butyl 3-amino-2,3,4,5-tetrahydro-2-oxo-1H-1-benzazepine-1-acetate with a melting point of 117 to 118° C. were obtained. 2.9 g of the amine obtained above and 3.2 g of the acid obtained above under D) were dissolved in 100 ml of dichloromethane. 2.2 ml of N-methylmorpholine, 1.27 g of hydroxybenzotriazole and 3.81 g of N-ethyl-N'-(3-dimethylaminopropyl)carbodiimide hydrochloride were added to the reaction mixture while cooling in ice. The reaction mixture was then stirred at room temperature for one hour. For working up, the reaction mixture was diluted with dichloromethane and washed successively with water, aqueous potassium bisulfate solution, water, aqueous sodium bicarbonate solution and again with water. The organic phase was then dried over sodium sulfate and the solvent was evaporated off under reduced pressure. The resulting crude product was purified by column chromatography on silica gel under slightly elevated pressure (flash chromatography) using n-hexane/ethyl acetate, increasing the ethyl acetate content of the eluent during the elution from the initial 1:9 to 3:7. 5.4 g of the pure title compound were obtained as an oily product.

IR spectrum (as film): 3400 $cm^{-1}$, 1725 $cm^{-1}$, 1660 $cm^{-1}$

EXAMPLE 2

3-{1-[2'-(Ethoxycarbonyl)-4'-phenylbutyl]cyclopentane-1-carbonylamino}-2,3,4,5-tetrahydro-2-oxo-1H-1-benzazepine-1-acetic acid.

5 g of tert-butyl 3-{1-[2'-(ethoxycarbonyl)-4'-phenylbutyl]cyclopentane-1-carbonylamino}-2,3,4,5-tetrahydro-2-oxo-1H-1-benzazepine-1-acetate (see Example 1 for preparation) were dissolved in 16 ml of trifluoroacetic acid. The solution was stirred at room temperature for 3 hours. For working up, the trifluoroacetic acid was evaporated off under reduced pressure. The remaining residue was dissolved in dichloromethane, and the solution was washed with water until neutral. The organic phase was subsequently dried over sodium sulfate and evaporated under reduced pressure. The remaining residue was stirred several times with n-hexane and evaporated to dryness again each time. 3.4 g of the title compound were obtained as a solid foam with a melting range from 81° to 104° C.

EXAMPLE 3

Tert-butyl (3S,2'R)-3-{1-[2'-(ethoxycarbonyl)-4'-phenylbutyl]cyclopentane-1-carbonylamino}-2,3,4,5-tetrahydro-2-oxo-1H-1-benzazepine-1-acetate.

A) 30.5 g of 1-[2'-(Ethoxycarbonyl)-4'-phenylbutyl]cyclopentane-1-carboxylic acid (see Example 1D) for preparation) and 11.6 g of L-(−)-α-methylbenzylamine were dissolved in ethanol with heating. The reaction mixture was cooled in a refrigerator for 12 hours, and then the mass of crystals which had separated out was filtered out with suction, dried and recrystallized several times from ethanol (until the optical rotation was constant) and subsequently dried under reduced pressure. 17.7 g of an α-methylbenzylammonium salt of the above acid were obtained with a melting point of 118° to 121° C. and optical rotation $[\alpha]_D^{20}$=+5.6° (c=0.5 in methanol).

To liberate the acid, this salt was taken up in a water/dichloromethane mixture, and the mixture was acidified with aqueous potassium bisulfate solution. The organic phase was separated, and the aqueous phase was then extracted three times with dichloromethane. The combined organic extracts were washed with water, dried over sodium sulfate and evaporated under reduced pressure. The remaining residue was dried. 11.2 g of pure (2'R)-1-[2'-(ethoxycarbonyl)-4'-phenylbutyl]cyclopentane-1-carboxylic acid were obtained, optical rotation $[\alpha]_D^{20}$=+7.4° (c=0.651 in methanol).

B) A solution of 12.65 g of L-(+)-tartaric acid in 54 ml of ethanol heated to 65° C. was added to a solution, heated to 65° C., of 24.5 g of the racemic tert-butyl 3-amino-2,3,4,5-tetrahydro-2-oxo-1H-1-benzazepine-1-acetate (see Example 1I for preparation). The reaction mixture was stirred at room temperature for one hour. Then a solution of 1.72 ml of benzaldehyde in 1.3 ml of ethanol was added dropwise. The resulting suspension was refluxed at 80° C. for 14 hours and then cooled to room temperature. The resulting crystalline precipitate was filtered out with suction, taken up in 80 ml of ethanol and again refluxed for 8 hours. It was then cooled to room temperature and the crystals were filtered out with suction and dried under reduced pressure at 50° C. 23.6 g of tartrate with a melting point of 195° to 196° C. and an optical rotation $[\alpha]_D^{20}$ of −152° (c=0.5 in methanol) were obtained. To liberate the base, 23.6 g of the tartrate were cooled in a mixture of 250 ml of water and 108 ml of dichloromethane to 0° C. with stirring, and the pH was adjusted to 9.6 by adding aqueous ammonia solution. The organic phase was separated, the aqueous phase was extracted once more with 30 ml of dichloromethane, and the organic phases were combined, dried over sodium sulfate and concentrated under reduced pressure. The remaining residue was crystallized from methyl tert-butyl ether and dried under reduced pressure. 12.2 g of tert-butyl (3S)-3-amino-2,3,4,5-tetrahydro-2-oxo-1H-1-benzazepine-1-acetate with a melting point of 113 to 115° C. and an optical rotation $[\alpha]_D^{20}$ of −276.2° (c=0.5 in methanol) were obtained.

C) 5.4 g of the acid prepared above under A) were dissolved in 60 ml of dried dichloromethane. The solution was mixed with 2.33 ml of triethylamine and cooled to −20° C. Then a solution of 1.31 ml of methanesulfonyl chloride in 5 ml of dried dichloromethane was slowly added dropwise. After stirring for 15 minutes, a solution of 4.8 g of the amine obtained above under B) and 2.33 ml of triethylamine in 60 ml of dichloromethane was added dropwise. The reaction mixture was subsequently stirred at room temperature for one hour. For working up, the reaction mixture was poured into water, and the organic phase was separated, washed with aqueous potassium bisulfate solution and subsequently with water, dried over sodium sulfate, filtered and concentrated under reduced pressure. The remaining crude product was purified by flash chromatography on 500 g of silica gel using n-hexane/ethyl acetate (7:3). Drying under reduced pressure resulted in 9.5 g of pure title compound as oil, optical rotation $[\alpha]_D^{20}=-115.2°$ (c=0.463 in methanol).

EXAMPLE 4

(3S,2'R)-3-{1-[2'-(Ethoxycarbonyl)-4'-phenylbutyl] cyclopentane-1-carbonylamino}-2,3,4,5-tetrahydro-2-oxo-1H-1-benzazepine-1-acetic acid.

9.4 g of tert-butyl (3S,2'R)-3-{1-[2'-(ethoxycarbonyl)-4'-phenylbutyl]cyclopentane-1-carbonylamino}-2,3,4,5-tetrahydro-2-oxo-1H-1-preparatine-1-acetate (see Example 3 for preparation) were dissolved in 15 ml of dichloromethane while cooling in ice. 31 ml of trifluoroacetic acid were added to the solution, and the reaction mixture was kept in a refrigerator at 4° C. for about 12 hours. For working up, the dichloromethane and the trifluoroacetic acid were evaporated off under reduced pressure. The resulting crude product was taken up in ethyl acetate and washed with water, dilute aqueous sodium bicarbonate solution and again with water. The organic phase was separated, dried over sodium sulfate and evaporated under reduced pressure. The remaining residue was purified by flash chromatography on silica gel, using as eluent initially dichloromethane and then dichloromethane/methanol (95:5). The resulting product was dried under reduced pressure at 80° C. for 2 days. 7.3 g of the pure title compound were obtained as a solid foam with a melting point of 71 to 74° C., optical rotation $[\alpha]_D^{20}=-131.0°$ (c=0.5 in methanol).

EXAMPLE 5

Tert-butyl 3-{1-[2'-(tert-butoxycarbonyl)-'-phenylbutyl]cyclopentane-1-carbonylamino}-2,3,4,5-tetrahydro-2-oxo-1H-1-benzazepine-1-acetate.

A) 118 g of tert-butyl dimethylphosphonoacetate were dissolved in 875 ml of dried dimethylformamide under a nitrogen atmosphere. 58.9 g of potassium tert-butoxide were added to the solution while cooling in ice. The reaction mixture was subsequently heated to 60° C. for a short time and then allowed to cool to room temperature. A solution of 104.9 g of phenethyl bromide in 110 ml of dimethylformamide was added dropwise to the reaction mixture. The reaction mixture was then heated at 60° C. for 2 hours. For working up, the dimethylformamide was substantially evaporated off under reduced pressure, and the remaining residue was dissolved in methyl tert-butyl ether. The solution was acidified with aqueous potassium bisulfate solution. The organic phase was then separated, washed with water, dried over sodium sulfate and evaporated under reduced pressure. The resulting crude product was purified by flash chromatography on 3 kg of silica gel using dichloromethane/methyl tert-butyl ether (4:1) as eluent. 105.1 g of pure tert-butyl 2-(dimethylphosphono)-4-phenyl-n-butyrate were obtained as an oily product.

B) 105.1 g of the product obtained above were dissolved in 705 ml of dried tetrahydrofuran under a nitrogen atmosphere. 28.4 g of paraformaldehyde were added to the solution. A solution of 32.5 g of potassium tert- butoxide in 100 ml of tetrahydrofuran was then slowly added dropwise. The reaction mixture was subsequently stirred for one hour. For working up, the reaction mixture was acidified with cold aqueous potassium bisulfate solution and diluted with methyl tert-butyl ether. The organic phase was then separated, washed with water, dried over sodium sulfate and concentrated under reduced pressure. The resulting crude product was purified by flash chromatography on 700 g of silica gel using an n-hexane/ethyl acetate (9:1). 47.0 g of tert-butyl α-(phenethyl)acrylate were obtained as a colorless oil.

C) 200 ml of a 1.6 molar solution of butyllithium in n-hexane were added dropwise to a solution, cooled to −50° C., of 50.2 ml of diisopropylamine in 450 ml of absolute tetrahydrofuran, and the reaction mixture was kept at 0° C. for a further 30 minutes. Subsequently, at this temperature, a solution of 16.2 ml of cyclopentanecarboxylic acid in 40 ml of absolute tetrahydrofuran was added dropwise. The reaction mixture was stirred at 0° C. for a further 2 hours. A solution of 38 g of the product obtained above under B) in 50 ml of absolute tetrahydrofuran was then slowly added to the mixture. The reaction mixture was stirred at 0° C. for a further 2 hours and then left to stand at −15° C. for several hours. For working up, the reaction mixture was acidified with saturated aqueous potassium bisulfate solution while cooling in ice and extracted three times with n-hexane. The combined organic phases were washed seven times with half-saturated aqueous sodium bicarbonate solution and subsequently with water, then dried over sodium sulfate and evaporated under reduced pressure. The resulting oily crude product was crystallized from ice-cold n-hexane. 41.9 g of pure crystalline 1-[2-(tert-butoxycarbonyl)-4-phenylbutyl]cyclopentane-1-carboxylic acid were obtained with a melting point of 75 to 77° C.

D) 3.3 g of the product obtained above, 2.7 g of tert-butyl 3-amino-2,3,4,5-tetrahydro-2-oxo-1H-1-benzazepine-1-acetate (see Example 1I) for preparation), 1.53 ml of N-methylmorpholine and 1.18 g of hydroxybenzotriazole were dissolved in 93 ml of absolute dichloromethane under a nitrogen atmosphere. 3.52 g of N-ethyl-N'-(3-dimethylaminopropyl)carbodiimide hydrochloride were added to this solution while cooling in ice. The reaction mixture was then stirred while cooling in ice for 2 hours. For working up, the reaction mixture was washed successively with water, aqueous potassium bisulfate solution, water, aqueous sodium bicarbonate solution and water again. The organic phase was dried over sodium sulfate and concentrated under reduced pressure. The remaining crude product was purified by flash chromatography on 200 g of silica gel using n-hexane/ethyl acetate (7:3) as eluent and was crystallized from methyl tert-butyl ether. 4.2 g of the pure title compound were obtained with a melting point of 110° to 114° C.

EXAMPLE 6

3-[1-(2'-Carboxy-4'-phenylbutyl)cyclopentane-1-carbonylamino]-2,3,4,5-tetrahydro-2-oxo-1H-1-benzazepine-1-acetic acid.

4.1 g of tert-butyl 3-{1-[2'-(tert-butoxycarbonyl)-4'-phenylbutyl]cyclopentane-1-carbonylamino}-2,3,4,5-tetrahydro-2-oxo-1H-1-benzazepine-1-acetate (see Example 5 for preparation) were dissolved in 13 ml of trifluoroacetic acid at a temperature of 4° C. with exclusion of moisture. The resulting solution was stirred at this temperature for a further 3 hours. For working up, the reaction mixture was concentrated under reduced pressure. To remove trifluoroacetic acid completely, the residue was mixed with dichloromethane and evaporated again several times. The resulting residue was then dissolved in dichloromethane, and the solution was washed with water, dried over sodium sulfate and concentrated under reduced pressure. The crude product remaining as residue was crystallized from dichloromethane. 2.7 g of the pure title compound were obtained with a melting point of 178° to 183° C.

EXAMPLE 7

Tert-butyl (3S,2'R)-3-{1-[2'-(tert-butoxycarbonyl)-4'-phenylbutyl]cyclopentane-1-carbonylamino}-2,3,4,5-tetrahydro-2-oxo-1H-1-benzazepine-1-acetate.

A) 68 g of 1-[2'-(tert-butoxycarbonyl)-4'-phenylbutyl] cyclopentane-1-carboxylic acid (see Example 5C) for preparation) and 23.5 ml of L-(−)-α-methylbenzylamine were dissolved in 200 ml of ethanol with heating. The reaction mixture was worked up as described in Example 3A). 32.2 g of an α-methylbenzylammonium salt of the above acid were obtained with a melting point of 118° to 119° C., optical rotation $[\alpha]_D^{20}=+9.2°$ in (c=0.5 in methanol). To liberate the acid, this salt was treated further by the process described in Example 3A). 23 g of (2'R)-1-[2'-(tert-butoxycarbonyl)-4'-phenylbutyl] cyclopentane-1-carboxylic acid were obtained with a melting point of 68° to 70° C., optical rotation $[\alpha]_D^{20}=+15.4°$ (c=0.5 in methanol).

B) 60.1 g of the acid obtained above were reacted with 50.3 g of tert-butyl (3S)-3-amino-2,3,4,5-tetrahydro-2-oxo-1H-1-benzazepine-1-acetate (see Example 3B) for preparation) by the method described in Example 3C), and the resulting reaction mixture was worked up as described in Example 3C). 94.3 g of the title compound were obtained as a foam, optical rotation $[\alpha]_D^{20}110.2°$ (c=0.5 in methanol).

IR Spectrum (as KBr disc): 3420 cm$^{-1}$, 1743 cm$^{-1}$, 1725 cm$^{-1}$, 1670 cm$^{-1}$

EXAMPLE 8

(3S,2'R)-3-[1-(2'-Carboxy-4'-phenylbutyl) cyclopentane-1-carbonylamino]-2,3,4,5-tetrahydro-2-oxo-1H-1-benzazepine-1-acetic acid.

93 g of tert-butyl (3S,2'R)-3-{1-[2'-(tert-butoxycarbonyl)-4'-phenylbutyl]cyclopentane-1-carbonylamino}-2,3,4,5-tetrahydro-2-oxo-1H-1-benzazepine-1-acetate (see Example 7 for preparation) were hydrolyzed with trifluoroacetic acid by the method described in Example 6, and the reaction mixture was worked up as described in Example 6. 63.5 g of the title compound were obtained as a solid foam with a melting range from 97° to 122° C., optical rotation $[\alpha]_D^{20}=-136.2°$ (c=0.5 in methanol)

EXAMPLE 9

Benzyl (3S,2'S)-3-{1-[2'-(tert-butoxycarbonyl)-3'-(2-methoxyethoxy)propyl]cyclopentane-1-carbonylamino}-3,4-dihydro-4-oxo-1,5-benzoxazepine-5(2H)-acetate.

A) 7 ml of sulfuric acid were added to a solution of 100 g of 3-bromopropionic acid in 200 ml of diethyl ether, and the reaction mixture was cooled to −20° C. Then 123 ml of liquified isobutene were added. The reaction mixture was stirred at room temperature in a pressure vessel for several hours. Subsequently, for working up, the reaction mixture was poured into dilute ice-cold aqueous sodium hydroxide solution. The ether phase was separated and the aqueous phase was extracted once more with ether. The combined organic phases were washed with aqueous sodium chloride solution, dried over sodium sulfate and evaporated under reduced pressure. The resulting crude product was distilled under reduced pressure. 100 g of tert-butyl 3-bromopropionate were obtained, boiling point (20)=75° to 77° C.

B) 50.4 ml of diisopropylamine were dissolved in 300 ml of absolute tetrahydrofuran under a nitrogen atmosphere, and the solution was cooled to −70° C. At this temperature, 200 ml of a 1.6 molar solution of butyl-lithium in n-hexane were slowly added dropwise to the solution. The reaction mixture was allowed to warm to 0° C., stirred at this temperature for 30 minutes and again cooled to −20° C. At this temperature, a solution of 16.2 ml of cyclopentanecarboxylic acid in 30 ml of absolute tetrahydrofuran was added dropwise. The reaction mixture was then stirred at room temperature for 2 hours. The mixture was subsequently cooled to −10° C. and slowly added dropwise to a solution, cooled to −10° C., of 35 g of tert-butyl 3-bromopropionate in 100 ml of tetrahydrofuran. The reaction mixture was stirred at room temperature for several hours. For working up, it was acidified with dilute aqueous hydrochloric acid solution and diluted with 375 ml of diethyl ether. The organic phase was separated, and the aqueous phase was extracted three more times with 100 ml of diethyl ether each time. The combined organic extracts were washed with aqueous sodium chloride solution, dried over sodium sulfate and evaporated under reduced pressure. The remaining residue was dissolved in 300 ml of diethyl ether. The solution was shaken six times with aqueous sodium bicarbonate solution and subsequently four times with 10% strength aqueous sodium carbonate solution. The combined sodium carbonate solutions were acidified while cooling in ice and extracted three times with 150 ml of ether each time. These ether extracts were combined with the ethereal solution, and the resulting solution was washed with aqueous sodium chloride solution, dried over sodium sulfate and concentrated under reduced pressure. The resulting crude product was crystallized from ice-cold n-hexane. 7.7 g of pure 1-[2-(tert-butoxycarbonyl)ethyl]-1-cyclopentanecarboxylic acid were obtained with a melting point of 78° to 81° C.

C) 30 ml of diisopropylamine were dissolved in 100 ml of absolute tetrahydrofuran under a nitrogen atmosphere, and the solution was cooled to −70° C. 132 ml of a 1.6 molar solution of butyllithium in n-hexane were added dropwise to the solution, and the reaction mixture was stirred at 0° C. for a further 30 minutes and then cooled again to −70° C. The reaction mixture was subsequently subjected to dropwise additions successively of a solution of 24.2 g of the product prepared above under B) in 100 ml of absolute tetrahydrofuran and then a solution of 14.2 ml of methoxyethoxymethyl chloride in 20 ml of absolute tetrahydrofuran. The reaction mixture was then stirred at room temperature for 16 hours. For working up, the reaction mixture was poured into an ice/water mixture, acidified with aqueous potassium bisulfate solution and extracted three times with 300 ml of ethyl acetate each time. The organic phases were combined, washed with aqueous sodium chloride solution, dried over sodium sulfate and concentrated under reduced pressure. The remaining crude product was purified by flash chromatography on 500 g of silica gel using dichloromethane/ether (8:2) as eluent. 26.5 g of pure 1-[2'-(tert-butoxycarbonyl)-3'-(2-methoxyethoxy)propyl] cyclopentane-1-carboxylic acid were obtained as an oil.

D) 36.7 g of the racemic acid obtained above were dissolved in 184 ml of n-hexane, and 18.4 g of (+)-pseudoephedrine were added to the solution. The precipitate which separated out was dissolved again by briefly boiling under reflux. The solution was then cooled and left to stand in a refrigerator for several hours. The crystalline precipitate which had formed was filtered out with suction, washed with ice-cold n-hexane and recrystallized four more times from n-hexane. 16.2 g of a pseudoephedrine salt of the above acid were obtained with a melting point of 89° to 91° C., optical rotation $[\alpha]_D^{20}$=+36.5° (c=1 in methanol)

To liberate the acid, 16 g of this salt were suspended in n-hexane, and the reaction mixture was acidified with ice-cold aqueous potassium bisulfate solution. The organic phase was separated, and the aqueous phase was extracted twice more with n-hexane. The combined organic phases were washed with aqueous sodium chloride solution, dried over sodium sulfate and evaporated under reduced pressure. The residue was dried at 50° C under reduced pressure. 9.9 g of (2'S)-1-[2'-(tert-butoxycarbonyl)-3'-(2-methoxyethoxy)propyl]cyclopentane-1-carboxylic acid were obtained as an oil, optical rotation $[\alpha]_D^{20}$=+2.9° (c=1 in methanol).

E) 17.2 g of sodium hydride (80%) were dissolved in 400 ml of dry dimethylformamide under a nitrogen atmosphere and with exclusion of moisture. A solution of 50 g of L-BOC-serine [N-(tert-butoxycarbonyl)serine]in 50 ml of dry dimethylformamide was slowly added dropwise to this solution at 0° C. The reaction mixture was allowed to warm slowly to 15° C., then a solution of 37.4 g of o-nitrophenol in 50 ml of dimethylformamide was added dropwise, and the reaction mixture was stirred at room temperature for several hours. For working up, the reaction mixture was poured into ice-cold aqueous potassium bisulfate solution. It was then extracted several times with ethyl acetate, and the combined organic phases were mixed with aqueous sodium bicarbonate solution. The aqueous phase was separated, washed with ether and subsequently acidified with potassium bisulfate solution and extracted with ethyl acetate. The ethyl acetate extract was washed with water, dried over sodium sulfate and evaporated under reduced pressure. 54.2 g of crude (2S)-3-(2-nitrophenoxy)-2-(tert-butoxycarbonyl-amino) propionic acid were obtained and were processed further without further purification.

F) 54.2 g of the acid obtained above were dissolved in 600 ml of methanol. 1.8 g of palladium catalyst (5% Pd/charcoal) were added to the solution. Hydrogenation was then carried out with a hydrogen pressure of 5 bar for 1 hour. The catalyst was subsequently filtered out, and the filtered solution was concentrated under reduced pressure. The resulting crude produced was crystallized from a methyl tert-butyl ether/n-hexane mixture while cooling in ice. 30.1 g of (2 S)-3-(2-aminophenoxy)-2-(tert-butoxycarbonylamino)propionic acid were obtained with a melting point of 87° to 91° C., optical rotation $[\alpha]_D^{20}$=+55.9° (c=1 in methanol).

G) 13.3 g of the acid obtained above were dissolved in 71 ml of dry dimethylformamide with exclusion of moisture. A solution of 7.8 ml of diethylphosphoryl cyanide in 6 ml of dimethylformamide was added to the solution while cooling in ice. After 10 minutes, 5.7 ml of triethylamine were added dropwise and the reaction mixture was stirred at room temperature for 1 hour. Then, for working up, the reaction mixture was poured into ice-water and extracted several times with methyl tert-butyl ether. The combined organic phases were dried and evaporated under reduced pressure. The crude product remaining as residue was crystallized from ethanol. 1.3 g of (3S)-3-(tert-butoxycarbonylamino)-2,3-dihydro-1,5-benzoxazepin-4 (5H)-one were obtained, optical rotation $[\alpha]_D^{20}$=−194° (c=1 in methanol).

H) 16 g of the product obtained above were dissolved in 313 ml of tetrahydrofuran with exclusion of moisture. A solution of 7.1 g of potassium tert-butoxide in 30 ml of tetrahydrofuran, and a solution of 10.9 ml of benzyl bromoacetate in 10 ml of tetrahydrofuran were successively added dropwise to the solution. The reaction mixture was stirred at room temperature for 1 hour. Subsequently, for working up, it was diluted with methyl tert-butyl ether and washed with water, and the organic phase was dried over sodium sulfate and concentrated under reduced pressure. The resulting crude product was purified by flash chromatography on 500 g of silica gel using n-hexane/ethyl acetate (3:2) as eluent. 0.5 g of pure benzyl (3S)-3-(tert-butoxycarbonylamino)-4-oxo-3,4-dihydro-1,5-benzoxazepine-5(2H)-acetate were obtained as an oil, optical rotation $[\alpha]_D^{20}$=−152° (c=0.68 in methanol).

I) 20 g of the product obtained above were dissolved in 137 ml of dichloromethane. 77 ml of trifluoroacetic acid were added to the solution, and the mixture was stirred for 1 hour. It was then concentrated under reduced pressure, the residue was dissolved in dichloromethane, and aqueous sodium bicarbonate solution was added until the reaction was alkaline. The organic phase was separated, washed with water, dried over sodium sulfate and concentrated under reduced pressure. 15.7 g of pure benzyl (3S)-3-amino-4-oxo-3,4-dihydro-1,5-benzoxazepine-5(2H)-acetate were obtained, optical rotation $[\alpha]_D^{20}$=−187.5° (c=0.536 in methanol).

J) 15.7 g of the product obtained above were dissolved in 48 ml of dry dichloromethane and, at room temperature, 1.6 g of the acid prepared above under D), 0.79 ml of N-methylmorpholine and 1.83 g of N-ethyl-N'-(3-dimethylaminopropyl)carbodiimide hydrochloride were added successively to the solution. The reaction mixture was then stirred at room temperature for 1 hour. Then, for working up, it was washed successively with water, aqueous potassium bisulfate solution, water, aqueous sodium bicarbonate solution and water again, dried over sodium sulfate and evaporated under reduced pressure. The crude product obtained as residue was purified by flash chromatography on silica gel using n-hexane/ether acetate (7:3) as eluent. 1.8 g of the title compound were obtained as an oil, optical rotation $[\alpha]_D^{20}$=−96.3° (c=0.326 in methanol).

EXAMPLE 10

Benzyl (3S,2'S)-3-{1-[2'-carboxy-3'-(2-methoxyethoxy)propyl]cyclopentane-1-carbonylamino}-4-oxo-3,4-dihydro-1,5-benzoxazepine-5(2H)-acetate.

1.6 g of benzyl (3S,2'S)-3-{1-[2'-(tert-butoxycarbonyl)-3'-(2-methoxyethoxy)propyl]cyclopentane-1-carbonylamino}-4-oxo-3,4-dihydro-1,5-benzoxazepine-5 (2H)-acetate. (See Example 9 for preparation) were dissolved in 5 ml of trifluoroacetic acid while cooling in ice. The solution was left to stand at a temperature of 4° C. for several hours. Subsequently, for working up, it was evaporated under reduced pressure, and the crude product remaining as residue was purified by flash chromatography on silica gel using dichloromethane/methyl tert-butyl ether/methanol (85:15:5). Drying resulted in 1.0 g of the title compound as an oil, optical rotation $[\alpha]_D^{20}$=−117.2° (c=0.42 in methanol)

EXAMPLE 11

(3S,2'S)-3-{1-[2'-Carboxy-3'-(2-methoxyethoxy)propyl]cyclopentane-1-carbonylamino}-4-oxo-3,4-dihydro-1,5-benzoxazepine-5(2H)-acetic acid.

0.95 g of benzyl (3S,2'S)-3-{1-[2'-carboxy-3'-(2-methoxyethoxy)propyl]cyclopentane-1-carbonylamino}-4- oxo-3,4-dihydro-1,5-benzoxazepine-5(2H)-acetate. (See Example 10 for preparation) was dissolved in 50 ml of ethanol. 0.2 g of palladium catalyst (Pd/charcoal 5%) was added to the solution. It was then hydrogenated under a pressure of 5 bar of hydrogen for 2 hours. For working up, the catalyst was filtered out, the filtered solution was evaporated under reduced pressure, and the remaining residue was dried. 0.7 g of the title compound was obtained as a foam-like product, optical rotation $[\alpha]_D^{20}=-142.6°$ (c=0 5 in methanol).

EXAMPLE 12

Tert-butyl (3R)-3-{1-[2'-(tert-butoxycarbonyl)-4'-(4-fluorophenoxy)butyl]cyclopentane-1-carbonylamino}-4-oxo-3,4-dihydro-1,5-benzothiazepine-5(2H)-acetate.

A) 20.5 g of tert-butyl dimethylphosphonoacetate were reacted with 25 g of 4-fluorophenoxyethyl bromide by the method described in Example 5 A). The reaction mixture was worked up as described in Example 5 A). 20.4 g of tert-butyl 4-(4-fluorophenoxy)-2-(dimethylphosphono)-n-butyrate were obtained.

B) 20.4 g of the product obtained above were reacted with 4.8 g of paraformaldehyde by the method described in Example 5 B). The reaction mixture was worked up as described in Example 5 B). 15.3 g of oily tert-butyl α-[2-(4-fluorophenoxy) ethyl]acrylate were obtained as crude product. This was further processed in the next stage without further chromatographic purification.

C) 15.3 g of the product obtained above were reacted with 5.1 ml of cyclopentanecarboxylic acid by the method described in Example 5 C). The reaction mixture was worked up as described in Example 5 C). 6.0 g of 1-[2'-(tert-butoxycarbonyl)-4'-(4-fluorophenoxy)butyl] cyclopentane-1-carboxylic acid were obtained with a melting point of 58°14 63° C. and a further 7.6 g of oily, still slightly contaminated product.

D) A solution of 122.4 g of N-acetyl-L-cysteine and 181.9 g of sodium bicarbonate in 550 ml of water was added to a solution of 100 ml of 1-fluoro-2-nitrobenzene in 1800 ml of ethanol. The reaction mixture was refluxed for 3 hours, then cooled to room temperature and filtered to remove precipitate. The filtrate was concentrated to about 700 ml, and the remaining residue was taken up in 1.8 l of water. The aqueous phase was extracted with diethyl ether and subsequently adjusted to pH 1 by adding concentrated aqueous hydrochloric acid solution. A yellow solid precipitated and was filtered out with suction. 253.6 g of crude R-(2-nitrophenyl)-N-acetyl-L-cysteine were obtained and were further processed without further purification.

E) 253.6 g of the product obtained above were mixed with 825 ml of 18 molar sulfuric acid and 3.3 l of water. The reaction mixture was refluxed for 40 minutes and then cooled to 0° C. 1925 ml of concentrated aqueous ammonia solution were added. The solid which then precipitated was filtered out with suction and recrystallized from water. 143 g of R-(2-nitrophenyl)-L-cysteine were obtained.

F) 100 g of the product obtained above and 62.2 g of potassium carbonate were dissolved in 7 liters of water. Subsequently 120 g of carbethoxyphthalimide were added in portions over the course of 3 hours, and the reaction mixture was stirred for a further 5 hours and then left to stand for several hours. The precipitated solid was subsequently filtered out with suction, and the filtrate was adjusted to a pH of 2 to 3 with concentrated aqueous hydrochloric acid solution. The precipitate which then separated out was filtered out with suction, washed several times with water and subsequently suspended in about 1l of ethanol with gentle heating (about 40° C.). After cooling, the solid was filtered out with suction and dried in air. 100 g of (2R)-3-(2-nitrophenylthio)-2-phthalimidopropionic acid were obtained and were further processed without further purification.

G) 100 g of the product obtained above were suspended in 1.5 liters of methanol. 0.8 g of palladium/charcoal (5%) catalyst was added to this, and the reaction mixture was hydrogenated for 5 hours. The catalyst was subsequently removed and the solvent was evaporated under reduced pressure. 71.6 g of crude (2R)-3-(2-aminophenylthio)-2-phthalimidopropionic acid were obtained as a yellowish brown oil which was further processed without further purification.

H) 71.6 g of the product obtained above were dissolved in dimethylformamide. 38.0 g of 1-[3-(dimethylamino)-propyl]-3-ethylcarbodiimide hydrochloride were added to the solution, and the reaction mixture was stirred at room temperature for 3 hours. The reaction mixture was subsequently diluted with 1.5 liters of ethyl acetate and extracted several times with 1.5 liter portions of 1N aqueous sodium bicarbonate solution. The organic phase was subsequently washed twice with 200 ml of water each time, dried over magnesium sulfate and evaporated to dryness under reduced pressure. The residue was purified by flash column chromatography using ethyl acetate/cyclohexane (1:1) as eluent. 46.3 g of (3R)-2,3-dihydro-3-phthalimido-1,5-benzothiazepin-4(5H)-one were obtained.

I) 10.6 g of powdered potassium hydroxide and 4.8 g of tetrabutylammonium bromide were added to a solution of 46.3 g of the product obtained above in 300 ml of tetrahydrofuran. The reaction mixture was cooled to 0° C. and then 23.2 ml of tert-butyl bromoacetate were slowly added dropwise. The reaction mixture was then stirred at room temperature for a further 3 hours. It was then filtered, and the filtrate was evaporated to dryness under reduced pressure. The residue was taken up in diethyl ether, and the ether phase was washed with water and 1 molar potassium bisulfate solution, dried over magnesium sulfate and subsequently concentrated under reduced pressure. The remaining oily crude product was mixed with ethyl acetate and diethyl ether. The precipitate which formed was filtered out with suction. 34 g of (3R)-5-(tert-butoxycarbonylmethyl)-2,3-dihydro-3-phthalimido-1,5-benzothiazepin-4(5H)-one were obtained as a solid. Concentration of the mother liquor under reduced pressure resulted in a further 25 g of slightly impure oily product. Optical rotation $[\alpha]_D^{20}=-146°$ (c=0.8 in dichloromethane).

J) 2 g of the product obtained above were mixed with 7.5 ml of ethanolamine, and the mixture was stirred at 80° C. for 10 minutes. The source of heat was subsequently removed, and the mixture was then stirred for a further 30 minutes. Then, for working up, the reaction mixture was mixed with 70 ml of 5% strength aqueous sodium chloride solution, and the resulting mixture was extracted with toluene. The organic phase was separated, dried over sodium sulfate and evaporated to dryness under reduced pressure. 1.46 g of crude tert-butyl (3R)-3-amino-4-oxo-3,4-dihydro-1,5-benzothiazepine-5(2H)acetate were obtained as toluene-containing solid.

K) 1.45 g of the above product, 1.75 g of the cyclopentanecarboxylic acid derivative obtained under C), 0.70 g of hydroxybenzotriazole and 1.50 ml of N-methylmorpholine were added to 100 ml of dry dichloromethane. The reaction mixture was then cooled to 0° C., and 1.76 g of 1-ethyl-3-(3-dimethylaminopropyl) carbodiimide hydrochloride were added, and the reaction mixture was stirred at room temperature for a further 5 hours. For working up, the reaction mixture was mixed with 1 molar potassium bisulfate solution, and the organic phase was separated and washed with 1 molar potassium bicarbonate solution and saturated sodium chloride solution, dried over sodium sulfate and evaporated to dryness under reduced pressure. The resulting crude product was purified by flash column chromatography using n-hexane/ethyl acetate (4:1) as eluent. 1.9 g of the title compound were obtained as an oil.

IR Spectrum (as film): 3366 cm$^{-1}$, 3059 cm$^{-1}$, 2969 cm$^{-1}$, 2874 cm$^{-1}$, 1727 cm$^{-1}$, 1657 cm$^{-1}$, 1505 cm$^{-1}$.

EXAMPLE 13

(3R)-3-{1-[2'-Carboxy-4'-(4-fluorophenoxy)butyl]cyclopentane-1-carbonylamino}-4-oxo-3,4-dihydro-1,5-benzothiazepine-5(2H)-acetic acid.

1.9 g of tert-butyl (3R)-3-{1-[2'-(tert-butoxycarbonyl)-4'-(4-fluorophenoxy)butyl]cyclopentane-1-carbonylamino}-4-oxo-3,4-dihydro-1,5-benzothiazepine-5(2H)-acetate (See Example 12 for preparation) were hydrolyzed with trifluoroacetic acid by the method described in Example 6. The reaction mixture was worked up as described in Example 6. 0.56 g of the title compound was obtained as an amorphous solid having a melting point of 90°–94° C.

EXAMPLE 14

Tert-butyl (3R)-3-{1-[2'-(tert-butoxycarbonyl)-5'-(3,4-dimethoxyphenyl)pentyl]cyclopentane-1-carbonylamino}-4-oxo-3,4-dihydro-1,5-benzothiazepine-5(2H)-acetate.

A) 6.7 g of triphenylphosphine were dissolved in 200 ml of acetonitrile. After the solution had been cooled to 0° C., 1.3 ml of bromine were added dropwise. The cooling bath was then removed and a solution of 5 g of 3-(3,4-dimethoxyphenyl)-1-propanol in 80 ml of acetonitrile was added dropwise. The reaction mixture was subsequently heated under reflux, using a water trap to remove 10 ml of distillate on several occasions over the course of 6 hours, replacing the amount removed with fresh acetonitrile. For working up, the solvent was evaporated off under reduced pressure, and the remaining residue was taken up in diethyl ether and filtered. The filtrate was concentrated under reduced pressure and purified by flash column chromatography using cyclohexane/methyl tert-butyl ether (7:2). 5.5 g of 3-(3,4-dimethoxyphenyl)-1-bromopropane were obtained as a colorless oil.

B) 5.5 g of the product obtained above were reacted with 3.8 ml of tert-butyl dimethylphosphonoacetate by the method described in Example 5 A). The reaction mixture was worked up as described in Example 5 A). 6.1 g of tert-butyl 4-(3,4-dimethoxyphenyl)-2-(dimethylphosphono)valerate were obtained as a colorless oil.

C) 6 g of the product obtained above were reacted with paraformaldehyde by the method described in Example 5 B). The reaction mixture was worked up as described in Example 5 B). The resulting crude product was purified by flash column chromatography using methyl tert-butyl ether/cyclohexane (1:3) as eluent. 3.4 g of oily tertbutyl 1-[3-(3,4-dimethoxyphenyl)propyl]acrylate were obtained.

D) 3.4 g of the product obtained above were reacted with 1.3 ml of cyclopentane carboxylic acid by the method described in Example 5 C). The reaction mixture was worked up as described in Example 5 C). The crude product was purified by flash column chromatography using ethyl acetate/cyclohexane (1:3) as eluent. 2.5 g of oily 1-[2-(tert-butoxycarbonyl)-5-(3,4-dimethoxyphenyl)pentyl]cyclopentanecarboxylic acid were obtained.

E) 2.5 g of the product obtained above were dissolved in 50 ml of acetonitrile. At a temperature of 0° C. and with exclusion of moisture, 4.2 ml of diisopropylethylamine, 1.7 g of 2-chloro-1-methylpyridinium iodide and 2.5 g of tert-butyl (3R)-3-amino-4-oxo-3,4-dihydro-1,5-benzodiazepine-5(2H)-acetate (see Example 12 J for preparation) were successively added to the solution. The reaction mixture was then stirred at 0° C. for 30 minutes and at room temperature for 2 hours. For working up, the reaction mixture was evaporated to dryness under reduced pressure, and the remaining residue was dissolved in dichloromethane. The solution was shaken first with dilute aqueous hydrochloric acid solution and then with water. The organic phase was separated, and the aqueous phase was extracted twice more with dichloromethane. The combined organic phases were subsequently dried over sodium sulfate and concentrated under reduced pressure. 3 g of the title compound were obtained as an oily residue.

Thin-layer chromatography on silica gel: Rf=0.4 (eluent cyclohexane/ethyl acetate 1:1)

EXAMPLE 15

(3R)-3-{1-[2'-Carboxy-5'-(3,4-dimethoxyphenyl)pentyl]cyclopentane-1-carbonylamino}-4-oxo-3,4-dihydro-1,5-benzothiazepine-5(2H)-acetic acid.

3 g of tert-butyl (3R)-3-{1-[2'-tert-butoxycarbonyl)-5'-(3,4-dimethoxyphenyl)pentyl]cyclopentane-1-carbonylamino}-4-oxo-3,4-dihydro-1,5-benzothiazepine-5(2H)-acetate (see Example 14 for preparation) were dissolved in 20 ml of dichloromethane. 3 ml of trifluoroacetic acid were added to the solution, and the reaction mixture was stirred at room temperature for 2 days. For working up, the reaction mixture was concentrated under reduced pressure. To remove the trifluoroacetic acid completely, the residue was mixed with 2 ml portions of toluene and evaporated again several times. The crude product obtained in this way was purified by flash chromatography on silica gel, using as eluent initially dichloromethane/ethyl acetate 1:1 and then pure ethyl acetate. Concentration of the eluate under reduced pressure resulted in 1.26 g of the title compound as amorphous solid.

IR Spectrum (as KBr disc): 3365 cm$^{-1}$, 2942 cm$^{-1}$, 1726 cm$^{-1}$, 1652 cm$^{-1}$.

EXAMPLE 16

Benzyl 3-{1-[2'-(tert-butoxycarbonyl)-4'-phenylbutyl]cyclopentane-1-carbonylamino}-2,3,4,5-tetrahydro-2-oxo-1H-1-benzazepine-1-acetate.

A) 10.5 g of tert-butyl 3-amino-2,3,4,5-tetrahydro-2-oxo-1H-1-benzazepine-1-acetate (see Example 1I) for preparation), 8.25 g of p-toluenesulfonic acid hydrate and 20.1 ml of benzyl alcohol were added to 174 ml of toluene. The reaction mixture was boiled with a water trap for 4 hours, during which a precipitate which originally separated out slowly dissolved. The toluene was then stripped off under reduced pressure, and the remaining residue was stirred with methyl tert-butyl ether and then filtered out. The resulting solid residue was dissolved in dichloromethane, and the solution was made alkaline by adding aqueous sodium carbonate solution while cooling in ice. The dichloromethane phase was then separated, washed with water, dried over sodium sulfate and evaporated. The resulting crude product was recrystallized from methyl tert-butyl ether for purification. 8.2 g of benzyl 3-amino-2,3,4,5-tetrahydro-2-oxo-1H-1-benzazepine-1-acetate were obtained with a melting point of 105° to 107° C.

B) 12.8 g of the product obtained above were reacted with 13.7 g of 1-[2'-(tert-butoxycarbonyl)-4-phenylbutyl]cyclopentane-1-carboxylic acid (see Example 5 C) for preparation) by the method described in Example 3 C). The reaction mixture was worked up as described in Example 3 C). 19.3 g of the title compound were obtained with a melting point of 118° to 123° C.

EXAMPLE 17

Benzyl 3-[1-(2'-carboxy-4'-phenylbutyl)cyclopentane-1-carbonylamino]-2,3,4,5-tetrahydro-2-oxo-1H-1-benzazepine-1-acetate.

15 g of benzyl 3-{1-[2-(tert-butoxycarbonyl)-4-phenylbutyl]cyclopentane-1-carbonylamino}-2,3,4,5-tetrahydro-2-oxo-1H-1-benzazepine-1-acetate (see Example 16 for preparation) were reacted with 56 ml of trifluoroacetic acid by the method described in Example 6. The reaction mixture was worked up as described in Example 6, and the resulting crude product was crystallized from methyl tert-butyl ether. 13.1 g of the title compound were obtained with a melting point of 86° to 90° C.

EXAMPLE 18

Benzyl 3-{1-[2'-(tert-butylcarbonyloxymethoxycarbonyl)-4-phenylbutyl]cyclopentane-1-carbonylamino}-2,3,4,5-tetrahydro-2-oxo-1H-1-benzazepine-1-acetate.

2 g of benzyl 3-[1-(2'-carboxy-4'-phenylbutyl)cyclopentane-1-carbonylamino]-2,3,4,5-tetrahydro-2-oxo-1H-1-benzazepine-1-acetate (see Example 17 for preparation) were dissolved in 20 ml of dry dichloromethane with exclusion of moisture. 0.46 ml of triethylamine and 0.1 g of dimethylaminopyridine were added to the solution. Then, while cooling in ice, a solution of 0.5 g of chloromethyl pivolate in 3 ml of dry dichloromethane was added dropwise. The reaction mixture was subsequently stirred at room temperature for 2 days. For working up, the reaction mixture was poured into water, and the organic phase was separated, washed with aqueous sodium bicarbonate solution and subsequently with water, dried over sodium sulfate and concentrated under reduced pressure. The crude product which remained as a residue was purified by flash chromatography on 150 g of silica gel, using as eluent an n-hexane/ethyl acetate mixture with a composition initially of 7:3 and then of 1:1. 1.1 g of pure benzyl 3-{1-[2'-(pivaloyloxymethoxycarbonyl)-4'-phenylbutyl]cyclopentane-1-carbonylamino}-2,3,4,5-tetrahydro-2-oxo-1H-1-benzazepine-1-acetate were obtained as a solid foam with a melting range of 71°–78° C.

EXAMPLE 19

3-{1-[2'-(pivaloyloxymethoxycarbonyl)-4'-phenylbutyl]cyclopentane-1-carbonylamino}-2,3,4,5-tetrahydro-2-oxo-1H-1-benzazepine-1-acetic acid.

1.0 g of benzyl 3-{1-[2'-(pivaloyloxymethoxycarbonyl)-4'-phenylbutyl]cyclopentane-1-carbonylamino}-2,3,4,5-tetrahydro-2-oxo-1H-1-benzazepine-1-acetate (see Example 18 for preparation) was dissolved in 100 ml of ethanol. 0.5 g of palladium/charcoal catalyst (5%) was added to the solution. It was then hydrogenated under a pressure of 5 bar of hydrogen for 3 hours. For working up, the catalyst was filtered out, and the filtered solution was evaporated. The resulting residue was dried under reduced pressure at 80° C. 0.7 g of the title compound was obtained as a glass-like product.

IR Spectrum (as KBr disc): 3410 $cm^{-1}$, 1750 $cm^{-1}$, 1660 $cm^{-1}$

The compounds of formula I listed in following Table I can also be prepared by the processes described in the foregoing examples.

TABLE I

| Ex. No. | $R^1$ | $R^2$ | $R^3$ | $R^4$ | $R^5$ | A | Steric assignment in position C-s | C-r | Notes MP = melting range in °C. IR spectrum in KBr Bands in $cm^{-1}$ |
|---|---|---|---|---|---|---|---|---|---|
| 20 | phe-$CH_2$—$CH_2$— | H | H | H | H | $CH_2$ | rac | rac | ac, foam, mp: 79–95 |
| 21 | $CH_3$—O—$(CH_2)_2$—O—$CH_2$— | H | H | H | H | $CH_2$ | rac | rac | ac, oil IR: 3400, 2950, 1730, 1660 |
| 22 | $CH_3$—O—$(CH_2)_2$—O—$CH_2$— | H | H | H | H | $CH_2$ | S | S | ac, foam, mp: 60–66 |
| 23 | phe-$CH_2$—$CH_2$— | H | H | H | H | $CH_2$ | rac | S | ac, foam, mp: from 113 |
| 24 | nap-$CH_2$—$CH_2$— | H | H | H | H | $CH_2$ | rac | rac | ac, oil IR: 2949, 1726, 1632, 1195 |
| 25 | phe-O—$(CH_2)_3$— | H | H | H | H | $CH_2$ | rac | rac | ac, oil IR: 2951, 1726, 1634, 1241 |
| 26 | 4-F-phe-O—$CH_2$—$CH_2$— | H | H | H | H | $CH_2$ | rac | rac | ac, mp: 136–138 |
| 27 | phe-$CH_2$— | H | H | H | H | $CH_2$ | rac | rac | ac, mp: 216–217 |
| 28 | phe-$CH_2$—$CH_2$— | H | H | H | H | O | R | S | ac, oil IR: 3400, 2940, 1720, 1645 |

TABLE I-continued

| Ex. No. | R¹ | R² | R³ | R⁴ | R⁵ | A | C-s | C-r | Notes MP = melting range in °C. IR spectrum in KBr Bands in cm⁻¹ |
|---|---|---|---|---|---|---|---|---|---|
| 29 | phe-CH₂— | H | H | H | H | CH₂ | rac | S | ac, mp: 116–117 |
| 30 | 4-CH₃-phe-CH₂— | H | H | H | H | CH₂ | rac | rac | ac, mp: 223–225 |
| 31 | 4-F-phe-O—CH₂—CH₂— | Cl | Cl | H | H | S | rac | R | ac, mp: 98–102 |
| 32 | 4-CH₃O-phe-(CH₂)₃— | H | H | H | H | S | rac | R | ac, oil IR: 3366, 2943, 1725, 1653 |
| 33 | phe-CH₂—CH₂— | H | H | (CH₃)₃C | H | CH₂ | rac | rac | ac, mp: 195–196 |
| 34 | phe-CH₂—CH₂— | H | H | ind | H | CH₂ | rac | rac | ac, mp: 146–149 |
| 35 | phe-CH₂—CH₂— | H | H | diox | H | CH₂ | rac | rac | ac, oil IR: 3410, 2950, 1735, 1660 |
| 36 | phe-CH₂—CH₂— | H | H | phe | H | CH₂ | rac | rac | ac, mp: 108–111 |
| 37 | phe-CH₂—CH₂— | H | H | H | H | CH₂ | R | S | Na, mp: >270 |
| 38 | nap-CH₂— | H | H | H | H | CH₂ | rac | rac | ac, mp: 165–170 |
| 39 | nap-CH₂—CH₂— | H | H | H | H | CH₂ | R | S | ac, foam IR: 3402, 2949, 1723, 1633 |
| 40 | nap-CH₂—CH₂ | H | H | C₂H₅ | H | CH₂ | R | S | |

Notes to abbreviations used in table:
phe = phenyl,
nap = α-naphthyl,
ind = 5-indanyl,
diox = (2,2-dimethyl-1,3-dioxolan-4-yl)methyl,
C-s = asymmetric center in the side chain,
C-r = asymmetric center in the ring,
rac = racemic,
R = R configuration,
S = S configuration,
foam = resinous foam,
oil = oily,
ac = free acid,
Na = disodium salt.

EXAMPLE I

Tablets containing (3S,2'R)-3-{1-[2'-(ethoxycarbonyl)-4'-phenylbutyl]cyclopentane-1-carbonylamino}-2,3,4,5-tetrahydro-2-oxo-1H-1-benzazepine-1-acetic acid.

Tablets were produced with the following composition per tablet:

| | |
|---|---|
| (3S,2'R)-3-{1-[2'-(ethoxycarbonyl)-4'-phenylbutyl]cyclopentane-1-carbonylamino)-2,3,4,5-tetrahydro-2-oxo-1H-1-benzazepine-1-acetic acid. | 20 mg |
| Corn starch | 60 mg |
| Lactose | 135 mg |
| Gelatin (as 10% strength solution) | 6 mg |

The active substance, the corn starch and the lactose were converted into a paste with the 10% strength gelatin solution. The paste was comminuted, and the resulting granules were placed on a suitable plate and dried at 45° C. The dried granules were passed through a comminuting machine and mixed with the following further ancillary substances in a mixer:

| | |
|---|---|
| Talc | 5 mg |
| Magnesium stearate | 5 mg |
| Corn starch | 9 mg | and then compressed to 240 mg tablets.

EXAMPLE II

Injection solution containing (3S,2'R)-3-[1-(2'-carboxy-4'-phenylbutyl)cyclopentane-1-carbonylamino]-2,3,4,5-tetrahydro-2-oxo-1H-1-benzazepine-1-acetic acid.

An injection solution with the following composition per 5 ml was produced:

| | |
|---|---|
| (3S,2'R)-3-[1-(2'-carboxy-4'-phenylbutyl)cyclopentane-1-carbonylamino]-2,3,4,5-tetrahydro-2-oxo-1H-1-benzazepine-1-acetic acid | 10 mg |
| Na₂HPO₄.7H₂O | 43.24 mg |
| NaH₂PO₄.2H₂O | 7.72 mg |
| NaCl | 30.0 mg |
| Purified water | 4948.0 mg |

The solids were dissolved in water, and the solution was sterilized and dispensed in portions of 5 ml each into ampoules.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. A compound corresponding to the formula I $$R^4OOC-CH(R^1)-CH_2-C(\text{(CH}_2)_4\text{)}-CO-NH-CH(A-\text{aryl})-C(O)-N(CH_2-COOR^5)$$  I wherein R¹ is:
  a) a lower alkoxy-lower-alkyl group in which the lower alkoxy radical is substituted by a lower alkoxy group; or
  b) a phenyl-lower-alkyl or phenyloxy-lower-alkyl group, or a phenyl-lower-alkyl or phenyloxy-lower-alkyl group substituted in the phenyl ring by lower alkyl, lower alkoxy or halogen; or
  c) a naphthyl-lower-alkyl group;

A is $CH_2$, O or S, $R^2$ is hydrogen or halogen, $R^3$ is hydrogen or halogen, $R^4$ is hydrogen or a group forming a biolabile ester, and $R^5$ is hydrogen or a group forming a biolabile ester, or a physiologically acceptable acid addition salt thereof.

2. A compound according to claim 1, wherein at least one of $R^4$ and $R^5$ is a group forming a biolabile ester.

3. A compound according to claim 2, wherein the group forming a biolabile ester is a lower alkyl group, a phenyl group or phenyl-lower-alkyl group, a phenyl group or phenyl-lower-alkyl group substituted in the phenyl ring by lower alkyl or by a lower alkylene chain bonded to two adjacent carbon atoms, a dioxolanylmethyl group, a dioxolanylmethyl group substituted in the dioxolane ring by lower alkyl, a $C_2$–$C_6$-alkanoyloxymethyl group, or a $C_2$–$C_6$-alkanoyloxymethyl group substituted on the oxymethyl group by lower alkyl.

4. A compound according to claim 3, wherein the group forming a biolabile ester is a phenyl, benzyl or indanyl group or a (2,2-dimethyl-1,3-dioxolan-4-yl)-methyl group.

5. A compound according to claim 2, wherein $R^4$ is a group forming a biolabile ester, and $R^5$ is hydrogen.

6. A compound according to claim 1, wherein A is $CH_2$.

7. A compound according to claim 6, wherein $R^1$ is a phenylethyl group or a naphthylethyl group, and $R^2$ is hydrogen.

8. A pharmaceutical composition comprising an effective NEP-inhibiting amount of a compound according to claim 1, and at least one conventional pharmaceutical carrier or adjuvant.

9. A process for preparing a compound corresponding to the formula I

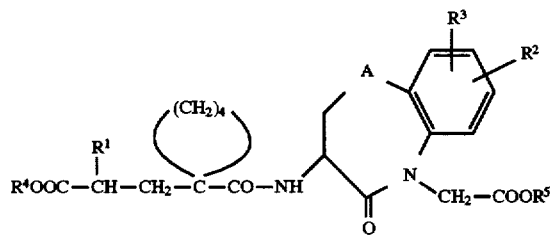

wherein $R^1$ is:
  a) a lower alkoxy-lower-alkyl group in which the lower alkoxy radical is substituted by a lower alkoxy group; or
  b) a phenyl-lower-alkyl group or phenyloxy-lower-alkyl group, or a phenyl-lower-alkyl group or phenyloxy-lower-alkyl group substituted in the phenyl ring by lower alkyl, lower alkoxy or halogen; or
  c) a naphthyl-lower-alkyl group, A is $CH_2$, O or S, $R^2$ is hydrogen or halogen, $R^3$ is hydrogen or halogen, $R^4$ is hydrogen or a group forming a biolabile ester, and $R^5$ is hydrogen or a group forming a biolabile ester, or a physiologically acceptable acid addition salt thereof, said process comprising the steps of:

reacting an acid corresponding to the formula II

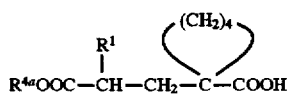

wherein $R^1$ has the above meaning, and $R^{4a}$ is an acid protective group, or a reactive acid derivative of a compound of formula II, with an amine corresponding to the formula III

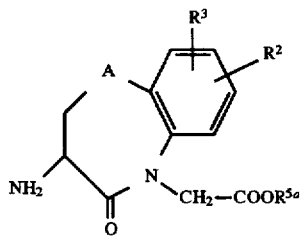

wherein $R^2$, $R^3$ and A have the above meanings, and $R^{5a}$ is an acid protective group, to yield an amide corresponding to formula IV

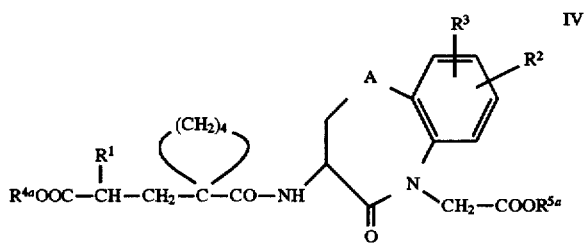

wherein $R^1$, $R^2$, $R^3$, $R^{4a}$, $R^{5a}$ and A have the above meanings, and if $R^{4a}$ and $R^{5a}$ in the compound of formula IV are acid protective groups not required for forming a biolabile ester, eliminating the acid protective groups.

10. A process according to claim 9, wherein said compound corresponding to formula I comprises at least one unblocked acid group, further comprising the step of esterifying the at least one unblocked acid group with an alcohol corresponding to the formula V $R^6$—OH 

or a reactive derivative corresponding to the formula Va $R^6$—X 

wherein $R^6$ is a group forming a biolabile ester, and X is a reactive group which can be eliminated.

11. A process according to claim 9, wherein if said compound corresponding to formula I is an acid, further comprising the step of converting the acid to a corresponding physiologically acceptable acid addition salt.

12. A process according to claim 9, wherein if said compound corresponding to formula I is a salt, further comprising the step of converting the salt to a corresponding free acid.

13. A process according to claim 9, wherein a plurality of acid protecting groups are eliminated simultaneously.

14. A process according to claim 9, wherein a plurality of acid protecting groups are eliminated successively.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
    ( A ) LENGTH: 17 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:1:

Asp Ile Ala Trp Phe Asn Thr Pro Glu His Val Val Pro Tyr Gly Leu
  1               5                   10                  15
  Gly ( 2 ) INFORMATION FOR SEQ ID NO:2:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:2:

Asp Ile Ala Trp
  1

( 2 ) INFORMATION FOR SEQ ID NO:3:

( i ) SEQUENCE CHARACTERISTICS:
    ( A ) LENGTH: 13 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:3:

Phe Asn Thr Pro Glu His Val Val Pro Tyr Gly Leu Gly
  1               5                   10